United States Patent
Klein et al.

(10) Patent No.: US 10,273,538 B2
(45) Date of Patent: Apr. 30, 2019

(54) ERROR-FREE SEQUENCING OF DNA

(71) Applicant: Fraunhofer-Gesellschaft zur Förderung der angewandten Forschung e.V., Munich (DE)

(72) Inventors: Christoph Klein, Regensburg (DE); Stefan Kirsch, Weinheim (DE); Zbigniew Tadeusz Czyz, Regensburg (DE); Urs Lahrmann, Regensburg (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 238 days.

(21) Appl. No.: 15/116,657

(22) PCT Filed: Feb. 5, 2015

(86) PCT No.: PCT/EP2015/052436
§ 371 (c)(1),
(2) Date: Aug. 4, 2016

(87) PCT Pub. No.: WO2015/118077
PCT Pub. Date: Aug. 13, 2015

(65) Prior Publication Data
US 2016/0348164 A1    Dec. 1, 2016

(30) Foreign Application Priority Data

Feb. 5, 2014   (EP) .................................... 14154044

(51) Int. Cl.
*C12Q 1/68*      (2018.01)
*C12P 19/34*     (2006.01)
*C12Q 1/6869*    (2018.01)

(52) U.S. Cl.
CPC .................................. *C12Q 1/6869* (2013.01)

(58) Field of Classification Search
None
See application file for complete search history.

(56) References Cited

U.S. PATENT DOCUMENTS

5,858,671 A    1/1999   Jones

FOREIGN PATENT DOCUMENTS

EP          2 042 602       4/2009
WO     WO 2012/042374      4/2012

OTHER PUBLICATIONS

Extended European Search Report issued in European Application No. 14154044.3, dated Jul. 14, 2014.
Monson-Miller et al., "Reference genome-independent assessment of mutation density using restriction enzyme-phased sequencing," *BMC Genomics*, 13(1):72, 2012.

(Continued)

*Primary Examiner* — Young J Kim
(74) *Attorney, Agent, or Firm* — Parker Highlander PLLC

(57) ABSTRACT

The invention relates to a novel method of error-free sequencing of DNA. Further, the present invention provides for a four-part oligonucleotide, comprising a fixed sequence, a randomized sequence, a restriction nuclease recognition site and/or restriction site, and a primer binding site. The invention also relates to the use of the sequenced DNA fragments obtained by the methods of the invention in methods for DNA sequence analysis, generation of cell lineage trees or assessment of copy numbers.

12 Claims, 14 Drawing Sheets

Figure 5:
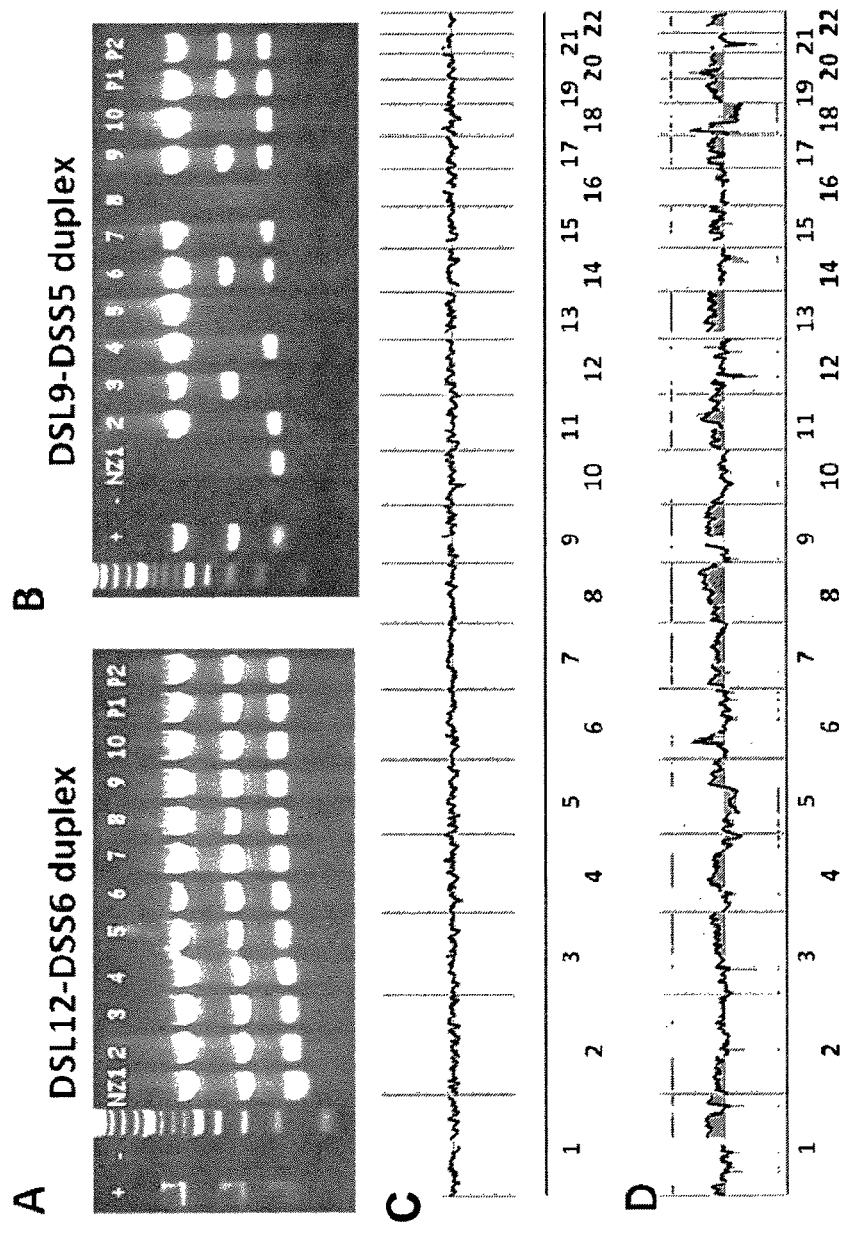

Specification includes a Sequence Listing.

(56) References Cited

OTHER PUBLICATIONS

PCT International Preliminary Report on Patentability issued in International Application No. PCT/EP2015/052436, dated Aug. 18, 2016.
PCT International Search Report and Written Opinion issued in International Application No. PCT/EP2015/052436, dated Jun. 11, 2015.

Figure 1

| Oligonucleotide type | n/m number | Oligoncucleotide sequence |
|---|---|---|
| $DSL_{12}$ | 12 | GCT AGG GAT AAC AGG GTA ATG C NNN NNN NNN NNN GTC AGT |
| $DSL_9$ | 9 | GCT AGG GAT AAC AGG GTA ATG C NNN NNN NNN GTC GT |
| $DSS_5$ | 5 | TA ACG ACdd |
| $DSS_6$ | 6 | TA ACT GACdd |
| DSPCR | | GCT AGG GAT AAC AGG GTA ATG C |

Figure 2

| Statistical measure | 2/3 PCRs positive | 3/3 PCRs positive |
|---|---|---|
| True positives | 35 | 29 |
| False negatives | 1 | 7 |
| True negatives | 34 | 36 |
| False positives | 2 | 0 |
| Sensitivity | 0.97 | 0.81 |
| Specificity | 0.94 | 1.0 |
| Positive predictive value | 0.95 | 1.0 |
| Negative predictive value | 0.97 | 0.84 |

Figure 3

| | N | Detected sequences in three marker QC assay | | | |
|---|---|---|---|---|---|
| | | 3/3 | 2/3 | 1/3 | 0/3 |
| Single WBC (unfixed) | 88 | 80 (90.9%) | 3 (3.41%) | 0 | 5 (5.68%) |
| Single WBC (CellSearch) | 189 | 73 (38.6%) | 51 (27.0%) | 20 (10.6%) | 45 (23.8%) |
| Single CTC (CellSearch) | 510 | 102 (20.0%) | 89 (17.5%) | 55 (10.8%) | 264 (51.8%) |

Figure 4

| Molecular assay | Analyzed cells[a] | Genomic integrity index (GII) | | | | | P Value chi-square |
|---|---|---|---|---|---|---|---|
| | | GII 0 | GII 1 | GII 2 | GII 3 | GII 4 | |
| PIK3CA HS1 | n = 383 | 7/23 (30.4%) | 14/25 (56.0%) | 48/62 (77.4%) | 102/117 (87.2%) | 146/156 (93.6%) | <0.0001 |
| PIK3CA HS2 | n = 383 | 8/23 (34.8%) | 18/25 (72.0%) | 55/62 (88.7%) | 109/117 (93.2%) | 149/156 (95.5%) | <0.0001 |
| PIK3CA complete | n = 383 | 4/23 (17.4%) | 12/25 (48.0%) | 45/62 (72.6%) | 97/117 (82.9%) | 141/156 (90.4%) | <0.0001 |
| HER2 qPCR | n = 351 | 3/12 (25.0%) | 8/18 (50.0%) | 41/61 (67.2%) | 95/112 (84.8%) | 136/148 (91.9%) | <0.0001 |
| aCGH | n = 50 | not assessed | not assessed | 4/5 (80.0%) | 7/9 (77.8%) | 36/36 (100%) | 0.016 |

Figure 9

A

GCTAGGGATAACAGGGTAATGCGTGGTCAGGGGGTCAGTTAAAGTAGTTTTGGCAAATTGGATAAAGAGTCA
AGACCCATCAGTGTGCTGTATTCAGGAGATCTCATGTGCAGAGACCACACATAGGCTCAAAATAAAAGGA
TGGAGGAAGATCTACCAAGCAAATGGAAAATCAAAAAGGCAGGGGTTGCAATCCTAGTCTCTGATAAAACAG
ACTTTATACCAACAAAGATCAAAAGAGACAAAGAAGGCCATTACATAATGGTAAAGAGATCAATTCAACAAGA
AGAGCTAACTATCCTAAATATATATGCACCCAATACAGGAGCACCCAGATTCATAAAGCAAGTCCTGAGTGAC
CTACAAAGAGACTTAGACTCCCAGACATTAAGTGACACTCTCGTCCTTGCAATTACCCTGTTATCCCTAGC

Annotation of the fragment: chr10, position 1811253 to 1811607

B

GCTAGGGATAACAGGGTAATGCGCGAAGGTAGGCGTCAGTTAACCAAGAAAAGAGGAGAGAAATACAAATAA
GCTCAATAAGGAACAAAACAGGAGAACATTACAACTGACACTATATAATACAAAAGATCATTCAAGGCTACTG
TGAACACCTTTACATGCATAAACTAAAATAGAAAAACTAAAGACATGGATAAATTCCTGGAAAGTAGAGAGGCATCA
CATTACCCAACTTCAAACTATACTATATAAGGCTATAGTCACCAACTCAGCATGGCACTGGTATAAAAATAGGCA
TGTAGACCAATGAAACAGAAAGAAGACAACCCAGATAAAGAAACATAAATCAGCCAACCAATCTTTGACAAGCAA
ACAAAAACATAAAGTGGGAAAGGACGCTCTATTCAACAAATGGTGCTGGATAATTGGCAGCCACATGTAG
AAGAATGAAACTGGATCCTCATCTCCCCTTTATACAAAATCAACACAAAATAGATAAAAGACTTAAGTGACCC
ACAAGGATAGGCCATTACCCTGTTATCCCTAGC

Annotation of the restriction fragment: chr5, position 96525427 to 96525889

C

GCTAGGGATAACAGGGTAATGCGTAGGAGAAAATGTCAGTTAAATCTATAAATTGTGTGCCACGTGCGGT
GGCTCATGACTGTAATCCCAGCACTTTGGGAGTCCGAGGTGGGCAGATGGGCAGGTGCAGAGTCAGGAGATTGAGAC
CATCTTGGCTAACACGGTGAAACCCCGTCTCTACTAAAAATACAAAAATTAGCCGGGTGAGGTGG
CAGGCACCTGTAGTCCCAGCTACTCCAGAGGCTGAGGTGAGAGAATGGCGTGAACCTGGGAGGCAGAGCT
TGCAGTGAGCTGAGATTGTGCCACTGCACTCCAGTCTGGGTGACAGAGCAAGACTCTGTCTCAAAAAAAA
AAAAAAAAAAATTCTATAAATTGTTGGGCAGTATGGCCTTTTTAAGTGACACTAAAGTCACAGC
ATTACCCTGTTATCCCTAGC

Annotation of the restriction fragment: chrX, position 94553619 to 94553978

Figure 10

| Step | Temp. | Time |
|---|---|---|
| Digestion | 42°C | 10 h |
| Inactivation | 80°C | 10 min |
|  | 4°C | ∞ |

Figure 11

| Step | Temp. | Time |
|---|---|---|
| Digestion | 37°C | 3 h |
| Inactivation | 65°C | 5 min |
|  | 4°C | ∞ |

Figure 12

| Temp. | Δ Temp./Cycle |
|---|---|
| 65°C → 15°C | -1°C/min |
| 15°C |  |

Figure 13

| Step | Temp. | Time |
|---|---|---|
| Ligation | 15°C | over night |

Figure 14

| Step | Temp. | Time |
|---|---|---|
| Fill-in | 68°C | 3 min |
| 1. PCR-Cycling 8x | 94°C | 40 sec |
|  | 57/60/63°C | 30 sec |
|  | 68°C | 1min 30sec +1sec/cycle |
| 2. PCR-Cycling 40x | 94°C | 40 sec |
|  | 57/60/63°C | 30 sec |
|  | 68°C | 1 min 45 sec +1sec/cycle |
| Final extension | 68°C | 3 min 40 sec |
|  | 4°C | ∞ |

Figure 15

| Step | Temp. | Time |
|---|---|---|
| Fill-in | 68°C | 3min |
|  | 80°C | 2 min |
| Addition of the Exonuclease I | 4°C |  |
|  | 37°C | 30 min |
|  | 85°C | 15 min |
| Addition of DSPCR primer |  | PAUSE |
| 1. PCR-Cycling 15x | 94°C | 40sec |
|  | 57°C | 30sec |
|  | 68°C | 1min 30sec +1sec/cycle |
| 2. PCR-Cycling 9x | 94°C | 40sec |
|  | 57°C +1°C/Z | 30sec |
|  | 68°C | 1min 45sec +1sec/cycle |
| 3. PCR-Cycling 23x | 94°C | 40sec |
|  | 65°C | 30sec |
|  | 68°C | 1min 53sec +1sec/cycle |
| Final extension | 68°C | 3min 40sec |
|  | 4°C | ∞ |

Figure 19a

```
    ReadID         Randomized                      chr6_124,934,321_124,934,396
                   sequence Reference                         TGGGAAG-T-GAGGCTGAGTGATTTAGGTATTTCCA-TA-TCAATAGCAAGACCACTGTGAGCTGAATACATCAGGTTATC
                                         X X                                                              X
IQ4WJ2H01EBTDI_GAAGAGGGG-AG       TGGGAAGGTAGAGGCTGAGTGATTTAGGTATTTCCAATAATCAATAGCAAGACCACTGTGAGCTGAATACATCGGGTTATC
IQ4WJ2H01DJ2RX_GAAGAGGGG-AG       TGGGAAG-T-GAGGCTGAGTGATTTAGGTATTTCCA-TAATCAATAGCAAGACCACTGTGAGCTGAATACATCGGGTTATC
IQ4WJ2H01EV3C9_GAAGAGGGG-AG       TGGGAAG-TAGAGGCTGAGTGATTTAGGTATTTCCAATAATCAATAGCAAGACCACTGTGAGCTGAATACATCGGGTTATC
IQ4WJ2H01D9VJ6_GAAGAGGGG-AG       TGGGAAG-T-GAGGCTGAGTGATTTAGGTATTTCCA-TA-TCAATAGCAAGACCACTGTGAGCTGAATACATCGGGTTATC
IQ4WJ2H01BDRUD_GAAGAGGGGGAG       TGGGAAG-T-GAGGCTGAGTGATTTAGGTATTTCCAATAATCAATAGCAAGACCACTGTGAGCTGAATACATCGGGTTATC
                                  ********** ** ******* * *************************** ****************************
                                                                          X X                                  X
IQ4WJ2H01DC2CL_ATGAGTGGGATA       TGGGAAG-T-GAGGCTGACTGATTTAGGTATTTCCA-TA-TCAATAGCAAGACCACTGTGAGCTGAATACATCAGGTTATC
IQ4WJ2H01AV527_ATGAGTGGGATA       TGGGAAG-T-GAGGCTGAGTGATTTAGGTATTTCCA-TA-TCAATAGCAAGACCACTGTGAGCTGAATACATCAGGTTATC
IQ4WJ2H01BN7XB_ATGAGTGGGATA       TGGGAAG-T-GAGGCTGAGTGATTTAGGTATTTCCA-TA-TCAATAGCAAGACCACTGTGAGCTGAATACATCAGGTTATC
IQ4WJ2H01AH386_ATGAGTGGGATA       TGGGAAG-T-GAGGCTGAGTGATTTAGGTATTTCCA-TA-TCAATAGCAAGACCACTGTGAGCTGAATACATCAGGTTATC
IQ4WJ2H01D63DR_ATGAGTGGGATA       TGGGAAG-T-GAGGCTGAGTGATTTAGGTATTTCCA-TA-TCAATAGCAAGACCACTGTGAGCTGAATACATCAGGTTATC
IQ4WJ2H01BVTHI_ATGAGTGGGATA       TGGGAAG-T-GAGGCTGAGTGATTTAGGTATTTCCA-TA-TCAATAGCAAGACCACTGTGAGCTGAATACATCAGGTTATC
IQ4WJ2H01BI7HX_ATGAGTGGGATA       TGGGAAG-T-GAGGCTGAGTGATTTAGGTATTTCCA-TA-TCAATAGCAAGACCACTGTGAGCTGAATACATCAGGTTATC
IQ4WJ2H02IESZE_ATGAGTGGGATA       TGGGAAG-T-GAGGCTGAGTGATTTAGGTATTTCCA-TA-TCAATAGCAAGACCACTGTGAGCTGAATACATCAGGTTATC
IQ4WJ2H02G69J5_ATGAGTGGGATA       TGGGAAG-T-GAGGCTGAGTGATTTAGGTATTTCCA-TA-TCAATAGCAAGACCACTGTGAGCTGAATACATCAGGTTATC
                                  ************ ****** * ***************************************************** ****
                                                                          X X                                  X
```

Figure 19b

```
    ReadID         Randomized                      chr22:39,277,551-39,277,608
                   sequence Reference                         CACTGCACTGTGAAATTCTGTGCCTCCGAAGACAGGCTCGCTATTTTTAGAAAGAGGG
                                          X
I935FME02I8EWU_GATAAATATGAA       CACTGCACCGTGAAATTCTGTGCCTC-GAAGACAGGCTCGCTATTTT-AGAA-GAGGG
I935FME02HST0F_GATAAATATGAA       CACTGCACCGTGAAATTCTGTGCCTCCGAAGACAGGCTCGCTATTTTTAGAAAGAGGG
I935FME02IS3DB_GATAAATATGAA       CACTGCACCGTGAAATTCTGTGCCTCCGAAGACAGGCTCGCTATTTTTAGAAAGAGGG
I935FME02GVA1A_GATAAATATGAA       CACTGCACCGTGAAATTCTGTGCCTCCGAAGACAGGCTCGCTATTTTTAGAAAGAGGG
I935FME02GV56X_GATAAATATGAA       CACTGCACCGTGAAATTCTGTGCCTCCGAAGACAGGCTCGCTATTTTTAGAAAGAGGG
I935FME02HT9UP_GATAAATATGAA       CÁCTGCACCGTGAAATTCTGTGCCTCCGAAGACAGGCTCGCTATTTTTAGAAAGAGGG
I935FME02IPW2U_GATAAATATGAA       CACTGCACCGTGAAATTCTGTGCCTCCGAAGACAGGCTCGCTATTTTTAGAAAGAGGG
I935FME02HNKYA_GATAAATATGAA       CACTGCACCGTGAAATTCTGTGCCTCCGAAGACAGGCTCGCTATTTTTAGAAAGAGGG
I935FME02IOS0E_GATAAATATGAA       CACTGCACCGTGAAATTCTGTGCCTCCGAAGACAGGCTCGCTATTTTTAGAAAGAGGG
I935FME02HXEG8_GATAAATATGAA       CACTGCACCGTGAAATTCTGTGCCTCCGAAGACAGGCTCGCTATTTTTAGAAAGAGGG
I935FME02JFTGT_GATAAATATGAA       CACTGCACCGTGAAATTCTGTGCCTCCGAAGACAGGCTCGCTATTTTTAGAAAGAGGG
I935FME02GBSUA_GATAAATATGAA       CACTGCACCGTGAAATTCTGTGCCTCCGAAGACAGGCTCGCTATTTTTAGAAAGAGGG
I935FME02GR861_GATAAATATGAA       CACTGCACCGTGAAATTCTGTGCCTCCGAAGACAGGCTCGCTATTTTTAGAAAGAGGG
I935FME02IPFUP_GATAAATATGAA       CACTGCACCGTGAAATTCTGTGCCTCCGAAGACAGGCTCGCTATTTTTAGAAAGAGGG
                                  ********* ************************ ****************** *****
                                          X
I935FME01C1GTK_AGACGTTTTAAG       CACTGCACTGTGAAATTCTGTGCCTCCGAAGACAGGCTCGCTATTTTTAGAAAGAGGG
I935FME01CN901_AGACGTTT-AAG       CACTGCACTGTGAAATTCTGTGCCTCCGAAGACAGGCTCGCTATTTTTAGAAAGAGGG
I935FME01EAK2C_AGACGTTTTAAG       CACTGCACTGTGAAATTCTGTGCCTCCGAAGACAGGCTCGCTATTTTTAGAAAGAGGG
I935FME01AXYNN_TAAATAGGGTTT       CACTGCACTGTGAAATTCTGTGCCTCCGAAGACAGGCTCGCTATTTTTAGAAAGAGGG
                                  ******* *** **********************************************
                                          X
```

Read "I935FME01AXYNN" was reverse mapped, i.e. it originated from the opposite strand of the other reads within its group and has therefore a different randomized sequence.

Figure 19c

```
ReadID          Randomized      chr22:18,455,108-18,455,137      chr22:18,455,218-18,455,247
                sequence Reference                       AGGTAAGGTGGTG-ACAACGGGTTTCCCAAA  ACAGGTGAACGGACGTACGGGAGTAGGGAC
                                             X                              X
I935FME02G3JAX_ AGCGGGGGTTGG    AGGTAAGGTGGTGAATAACGGGTTTCCCAAA  ------------------------------
I935FME02HPZCG_ AGCGGGGGTTGG    AGGTAAGGTGGTG-ATAACGGGTTTCCCAAA  ACAGGTGAACGGACGTACGGGAGTAGGGAC
I935FME02HEGF0_ AGCGGGGGTTGG    AGGTAAGGTGGTG-ATAACGGGTTTCCCAAA  ACA---------------------------
I935FME02FY2OL_ AGCGGGGGTTGG    AGGTAAGGTGGTG-ATAACGGGTTTCCCAAA  ACAGGTGAACGGACGTACGGGA--------
I935FME02FUAIM_ AGCGGGGGTTGG    AGGTAAGGTGGTG-ATAACGGGTTTCCCAAA  ACAGGTGAACGGACGTACGGGA--------
I935FME02HNVDR_ AGCGGGGGTTGG    AGGTAAGGTGGTG-ATAACGGGTTTCCCAAA  ACAGGTGAACGGACGTACGGGAGTAGGGAC
I935FME02GP6YE_ AGCGGGGGTTGG    AGGTAAGGTGGTG-ATAACGGGTTTCCCAAA  ACAGGTGAACGGACGTACGGGAGTAGGGAC
I935FME02IAAW2_ AGCGGGGGTTGG    AGGTAAGGTGGTG-ATAACGGGTTTCCCAAA  ACAGGTGAACGGACGTACGGGAGTAGGGAC
I935FME02I4UCC_ AGCGGGGGTTGG    AGGTAAGGTGGTG-ATAACGGGTTTCCCAAA  ACAGGTGAACGGACGTACGGGAGTAGGGAC
I935FME02FVCO0_ AGCGGGGGTTGG    AGGTAAGGTGGTG-ATAACGGGTTTCCCAAA  ACAGGTGAACGGACGTACGGGA--------
I935FME02JTEOX_ AGCGGGGGTTGG    AGGTAAGGTGGTG-ATAACGGGTTTCCCAAA  ACA---------------------------
I935FME02GYCTS_ AGCGGGGGTTGG    AGGTAAGGTGGTG-ATAACGGGTTTCCCAAA  ------------------------------
I935FME02HYT0N_ AGCGGGGGTTGG    AGGTAAGGTGGTG-ATAACGGGTTTCCCAAA  ACAGGTGAACGGACGTACGGGAGTA-----
I935FME02JBAVG_ AGCGGGGGTTGG    AGGTAAGGTGGTG-ATAACGGGTTTCCCAAA  ------------------------------
I935FME02FX9GA_ AGCGGGGGTTGG    AGGTAAGGTGGTG-ATAACGGGTTTCCCAAA  ACAGGTGAACGGACGTACGGGAGTAGGGAC
I935FME02GYYLN_ AGCGGGGGTTGG    AGGTAAGGTGGTG-ATAACGGGTTTCCCAAA  ------------------------------
I935FME02ID4XH_ AGCGGGGGTTGG    AGGTAAGGTGGTG-ATAACGGGTTTCCCAAA  ACAGGTGAACGGACGTACGGGAGTAGGGAC
I935FME02HVJJE_ AGCGGGGGTTGG    AGGTAAGGTGGTG-ATAACGGGTTTCCCAAA  ACAGGTGAACGGACGTACGGGAGTAGGGA-
I935FME02H32G2_ AGCGGGGGTTGG    AGGTAAGGTGGTG-ATAACGGGTTTCCCAAA  ACAGGTGAACGGACGTACGGGA--------
I935FME02F6Q0H_ AGCGGGGGTTGG    AGGTAAGGTGGTG-ATAACGGGTTTCCCAAA  ACAGGTGAACGGACGTACGGGAGTAGGGAC
I935FME02HNHHY_ AGCGGGGGTTGG    AGGTAAGGTGGTG-ATAACGGGTTTCCCAAA  ACAGGTGAACGGACGTACGGGAGTA-----
I935FME02FOIUY_ AGCGGGGGTTGG    AGGTAAGGTGGTG-ATAACGGGTTTCCCAAA  ACAGGTGAACGGACGTACGGGAGTAGGGAC
I935FME02GSN7O_ AGCGGGGGTTGG    AGGTAAGGTGGTG-ATAACGGGTTTCCCAAA  ------------------------------
I935FME02FR6XR_ AGCGGGGGTTGG    AGGTAAGGTGGTG-ATAACGGGTTTCCC---  ------------------------------
I935FME02IP2KO_ AGCGGGG-TTGG    AGGTAAGGTGGTG-ATAACGGGTTTCCCAAA  ACAGGTGAACGGACGTACGGCAGTAGCGAC
I935FME02JKE75_ AGCGGGG-TTGG    AGGTAAGGTGGTG-ATAACGGGTTTCCCAAA  ACAGGTGAACGGACGTACGGGAGTAGGGAC
                ******* ****    ************ ******************  ******************************
                                             X                              X
I935FME01AGM6X_ ATAGACTAGGCG    AGGTAAGGTGGTG-ACAACGGGTTTCCCAAA  ACAGGTGAACGGACATACGGGAGTAGGGAC
I935FME01AMWUD_ ATAGACTAGGCG    AGGTAAGGTGGTG-ACAACGGGTTTCCCAAA  ACAGGTGAACGGACATAC------------
I935FME01EEHFG_ ATAGACTAGGCG    AGGTAAGGTGGTG-ACAACGGGTTTCCCAAA  ACAGGTGAACGGACATACGGGAGTAGGGAC
I935FME01CP0EN_ ATAGACTAGGCG    AGGTAAGGTGGTG-ACAACGGGTTTCCCAAA  ACAGGTGAACGGACATACGGGA-TAGGGAC
I935FME01CAYQ8_ ATAGACTAGGCG    AGGTAAGGTGGTG-ACAACGGGTTTCCCAAA  ACAGGTGAACGGACATACGGGAGTAGGGAC
I935FME01CT2IH_ ATAGACTAGGCG    AGGTAAGGTGGTG-ACAACGGGTTTCCCAAA  ACAGGTGAACGGACATACGGGAGTAGGGAC
I935FME01BLNIO_ ATAGACTAGGCG    AGGTAAGGTGGTG-ACAACGGGTTTCCCAAA  ACAGGTGAACGGACATACGGGAGTAGGGAC
I935FME01EW5VF_ ATAGACTAGGCG    AGGTAAGGTGGTG-ACAACGGGTTTCCCAAA  ACAGGTGAACGGACATACGGGAGTAGGGAC
I935FME01BR9EW_ ATAGACTAGGCG    AGGTAAGGTGGTG-ACAACGGGTTTCCCAAA  ACAGGTGAACGGACATACGGGAGTAGGGAC
I935FME01D9HRR_ ATAGACTAGGCG    AGGTAAGGTGGTG-ACAACGGGTTTCCCAAA  ACAGGTGAACGGACATACGGGA-TAGGGAC
I935FME01DYFB5_ ATAGACTAGGCG    AGGTAAGGTGGTG-ACAACGGGTTTCCCAAA  ACAGGTGAACGGACATACGGGAGTAGGGAC
I935FME01D6FUV_ ATAGACTAGGCG    AGGTAAGGTGGTG-ACAACGGGTTTCCCAAA  ACAGGTGAACGGACATACGGGAGTAGGGAC
I935FME01BB15Y_ ATAGACTAGGCG    AGGTAAGGTGGTG-ACAACGGGTTTCCCAAA  ACAGGTGAACGGACATACGGGAGTAGGGAC
I935FME02IGF97_ ATAGACTAGGCG    AGGTAAGGTGGTG-ACAACGGGTTTCCCAAA  ACAGGTGAACGGACATACGGGAGTAGGGAC
I935FME02FLWO3_ ATAGACTAGGCG    AGGTAAGGTGGTG-ACAACGGGTTTCCCAAA  ACAGGTGAACGGACATACGGGAGTAGGGAC
I935FME02FOXSW_ ATAGACTAGGCG    AGGTAAGGTGGTG-ACAACGGGTTTCCCAAA  ACAGGTGAACGGACATACGGGAGTAGGGAC
I935FME02GUX6V_ ATAGACTAGGCG    AGGTAAGGTGGTG-ACAACGGGTTTCCCAAA  ACAGGTGAACGGACATGCGGGAGTAGGGAC
I935FME02GI4Z4_ ATAGACTAGGCG    AGGTAAGGTGGTG-ACAACGGGTTTCCCAAA  ACAGGTGAACGGACATACGGGAGTAGGGAC
I935FME02H2M7T_ ATAGACTAGGCG    AGGTAAGGTGGTG-ACAACGGGTTTCCCAAA  ACAGGTGAACGGACATACGGGAGTAGGGAC
I935FME02JHRO7_ ATAGACTAGGCG    AGGTAAGGTGGTG-ACAACGGGTTTCCCAAA  ACAGGTGAACGGACATACGGGAGTAGGGAC
I935FME01DYW8K_ ATAGACTAGGCG    AGGTAAGGTGGTG-ACAACGGGTTTCCCAAA  ACAGGTGAACGGACATACGGGAGTAGGGAC
I935FME01BFXU5_ ATAGACTAGGCG    AGGTAAGGTGGTG-ACAACGGGTTTCCCAAA  ACAGGTGAACGGACATACGGGAGTAGGGAC
I935FME02IQWMO_ ATAGACTAGGCG    AGGTAAGGTGGTG-ACAACGGGTTTCCCAAA  ACAGGTGAACGGACATACGGGAGTAGGGAC
I935FME02HQ894_ ATAGACTAGGCG    AGGTAAGGTGGTG-ACAACGGGTTTCCCAAA  ACAGGTGAACGGACATACGGGAGTAGGGAC
I935FME02JROVV_ ATAGACTAGGCG    AGGTAAGGTGGTG-ACAACGGGTTTCCCAGA  ACAGGTGAACGGACATACGGGAGTAGGGAC
                ************    ************* ***************  ***************** ***** *******
                                             X                              X
```

Figure 19d

```
ReadID          Randomized              chr22:42,820,701-42,820,754
                sequence Reference                       AAT-GGGCACTGTGCCTTGGTGGAGTTGGAAGGAATGA-TTTGTGTCTGGGAGGGG
                                X   XXX XX                            X       X       X
I935FME01DKBPG_ATATTTAAAGCT     TAT-CCCCTGTGTGCCTTGGTGGAGTTGGAAGGAATGA-TTTGTGTCTGGGAGGGG
I935FME01C29WR_ATATTTAAAGCT     TAT-CCCCTGTGTGCCTTGGTGGAGTTGGAAGGAATGA-TTTGTGTCTGGGAGGGG
I935FME01BLAFB_ATATTTAAAGCT     ------------------GGTGGAGTTGGAAGGAATGA-TTTGTGTCTGG-AGGGG
I935FME01AN93Y_ATATTTAAAGCT     ----CCCCTGTGTGCCTTGGTGGAGTTGGA-GGAATGA-TTTGTGTCTGGGAGGGG
I935FME01B80B0_ATATTTAAAGCT     TAT-CCCCTGTGTGCCTTGGTGGAGTTGGA-GGAATGA-TTTGTGTCTGG-AGGGG
I935FME01DFR9W_ATATTTAAAGCT     TAT-CCCCTGTGTGCCTTGGTGGAGTTGGA-GGAATGA-TTTGTGTCTGG-AGGGG
I935FME01BNPCR_ATATTTAAAGCT     TAT-CCCCTGTGTGCCTTGGTGGAGTTGGA-GGAATGA-TTTGTGTCTGG-AGGGG
I935FME01EO6UA_ATATTTAAAGCT     TATCCCCCTGTGTGCCTTGGTGGAGTTGGA-GGAATGA-TTTGTGTCTGG-AGGGG
I935FME01D7FI6_ATATTTAAAGCT     TAT-CCCCTGTGTGCCTTGGTGGAGTTGGAAGGAATGA-TTTGTGTCTGG-AGGGG
I935FME01B4QJQ_ATATTTAAAGCT     TAT-CCCCTGTGTGCCTTGGTGGAGTTGGAAGGAATGA-TTTGTGTCTGG-AGGGG
I935FME01AP8OU_ATATTTAAAGCT     TAT-CCCCTGTGTGCCTTGGTGGAGTTGGAAGGAATGA-TTTGTGTCTGG-AGGGG
I935FME01EGAYX_ATATTTAAAGCT     TAT-CCCCTGTGTGCCTTGGTGGAGTTGGAAGGAATGA-TTTGTGTCTGG-AGGGG
I935FME01C0Z0O_ATATTTAAAGCT     TAT-CCCCTGTGTGCCTTGGTGGAGTTGGAAGGAATGA-TTTGTGTCTGG-AGGGG
I935FME01A84M0_ATATTTAAAGCT     TAT-CCCCTGTGTGCCTTGGTGGAGTTGGAAGGAATGA-TTTGTGTCTGG-AGGGG
I935FME01CNOA1_ATATTTAAAGCT     TAT-CCCCTGTGTGCCTTGGTGGAGTTGGAAGGAATGA-TTTGTGTCTGG-AGGGG
I935FME01A1CI5_ATATTTAAAGCT     TAT-CCCCTGTGTGCCTTGGTGGAGTTG-A-GGAATGA-TTTGTGTCTGGGAGGGG
I935FME01AS8D7_ATATTTAAAGCT     ----CCCCTGTGTGCCTTGGTGGAGTTG-A-GGAATGA-TTTGTGTCTGG-AGGGG
I935FME01BJ137_ATATTTAAAGCT     TAT-CCCCTGTGTGCCTTGGTGGAGTTG-A-GGAATGA-TTTGTGTCTGG-AGGGG
I935FME01A46D0_ATATTTAAAGCT     TAT-CCCCTGTGTGCCTTGGTGGAGTTG-A-GGAATGA-TTTGTGTCTGG-AGGGG
                                ************ *** ********************* * ******* *********** *****
                                X   XXX XX                            X       X       X
I935FME01ENGKQ_ATGAATGCAGTT     --------TGTGTGCCTTGGTGGAGTTGGAAGGAGTGA-TTTGCGTCTGGGAGGGG
I935FME01A5DNG_ATGAATGCAGTT     --------TGTGTGCCTTGGTGGAGTTGGAAGGAGTGA-TTTGCGTCTGGGA-GGG
I935FME01C7OXZ_ATGAATGCAGTT     TAT-CCCCTGTGTGCCTTGGTGGAGTTGGAAGGAGTGA-TTTGCGTCTGGGA-GGG
I935FME01DB053_ATGAATGCAGTT     TAT-CCCCTGTGTGCCTTGGTGGAGTTGGAAGGAGTGA-TTTGCGTCTGGGA-GGG
I935FME01CU25R_ATGAATGCAGTT     TAT-CCCCTGTGTGCCTTGGTGGAGTTGGAAGGAGTGA-TTTGCGTCTGGGA-GGG
I935FME01AJLKP_ATGAATGCAGTT     TAT-CCCCTGTGTGCCTTGGTGGAGTTGGAAGGAGTGA-TTTGCGTCTGGGA-GGG
I935FME01B8P5R_ATGAATGCAGTT     TAT-CCCCTGTGTGCCTTGGTGGAGTTGGAAGGAGTGA-TTTGCGTCTGGGA-GGG
I935FME01BSJKW_ATGAATGCAGTT     TAT-CCCCTGTGTGCCTTGGTGGAGTTGGAAGGAGTGA-TTTGCGTCTGGGA-GGG
I935FME01DZ64B_ATGAATGCAGTT     TAT-CCCCTGTGTGCCTTGGTGGAGTTGGAAGGAGTGA-TTTGCGTCTGGGA-GGG
I935FME01EPZFR_ATGAATGCAGTT     ----------------TTGGTGGAGTTGGAAGGAGTGA-TTTGCGTCTGG-A-GGG
I935FME01ASAI7_ATGAATGCAGTT     ----------------TTGGTGGAGTTGGAAGGAGTGA-TTTGCGTCTGG-A-GGG
I935FME01C80EK_ATGAATGCAGTT     ----------------TTGGTGGAGTTGGAAGGAGTGA-TTTGCGTCTGG-AGGGG
I935FME01CN455_ATGAATGCAGTT     TAT-CCCCTGTGTGCCTTGGTGGAGTTGGAAGGAGTGA-TTTGCGTCTGG-AGGGG
I935FME01C304D_ATGAATGCAGTT     TAT-CCCCTGTGTGCCTTGGTGGAGTTGGAAGGAGTGA-TTTGCGTCTGG-AGGGG
I935FME01CGQON_ATGAATGCAGTT     TAT-CCCCTGTGTGCCTTGGTGGAGTTGGAAGGAGTGA-TTTGCGTCTGG-AGGGG
I935FME01EJQ9M_ATGAATGCAGTT     TAT-CCCCTGTGTGCCTTGGTGGAGTTGGAAGGAGTGA-TTTGCGTCTGG-AGGGG
I935FME01D218C_ATGAATGCAGTT     TAT-CCCCTGTGTGCCTTGGTGGAGTTGGAAGGAGTGA-TTTGCGTCTGG-AGGGG
I935FME01DCUU6_ATGAATGCAGTT     TAT-CCCCTGTGTGCCTTGGTGGAGTTGGAAGGAGTGA-TTTGCGTCTGG-AGGGG
I935FME01AI0RD_ATGAATGCAGTT     TAT-CCCCTGTGTGCCTTGGTGGAGTTGGAAGGAGTGA-TTTGCGTCTGG-AGGGG
I935FME01B6QGC_ATGAATGCAGTT     TAT-CCCCTGTGTGCCTTGGTGGAGTTGGAAGGAGTGA-TTTGCGTCTGG-AGGGG
I935FME01B6P77_ATGAATGCAGTT     TAT-CCCCTGTGTGCCTTGGTGGAGTTGGAAGGAGTGATTTTGCGTCTGG-AGGGG
I935FME01BRGZH_ATGAATGCAGTT     TAT-CCCCTGTGTGCCTTGGTGGAGTTGGAAGGAGTGA-TTTGCGTCTGG-AGGGG
I935FME01A2VKU_ATGAATGCAGTT     TAT-CCCCTGTGTGCCTTGGTGGAGTTGGAAGGAGTGA-TTTGCGTCTGG-AGGGG
                                ************ *** ******************************* *********** * ***
                                X   XXX XX                            X       X       X
```

All shown reads were reverse mapped to the reference.

ERROR-FREE SEQUENCING OF DNA

The invention relates to a novel method of error-free sequencing of DNA. Further, the present invention provides for a four-part oligonucleotide, comprising a fixed sequence, a randomized sequence, a restriction nuclease recognition site and/or restriction site, and a primer binding site. The invention also relates to the use of the sequenced DNA fragments obtained by the methods of the invention in methods for DNA sequence analysis, generation of cell lineage trees or assessment of copy numbers.

A number of documents including patent applications, manufacturer's manuals and scientific publications are cited herein. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Clinical applications such as pre-implementation molecular diagnostics, early detection of cancer and nucleic acid biomarkers-based longitudinal monitoring of therapy response require accurate sample preparation and whole genome amplification methods to provide sufficient high-quality DNA quantities for molecular analyses. A method for the amplification of DNA particularly useful for the amplification of the DNA or the whole genome of a single cell is described in WO 00/17390. However, whole genome amplification as well as sample preparation are prone to the introduction of errors in the DNA sequence. Thus, the assessment of correct sequences from single cells is hampered by high background level of sequencing errors. Therefore, a process to properly monitor and assess methodologically introduced sequence errors has to be established. The most important requirement to achieve this goal is to correctly retrieve the DNA sequences from single cells as they were before experimental manipulation. Current approaches use the information of the complementary DNA strand of each DNA sequence to correct for all changes that are not present in both strands of a original double stranded DNA molecule.

Various fundamentally distinct categories of approaches with significantly differing sensitivities have been used to separate sequence-error derived noise from real genetic variation in next-generation sequencing approaches. The first category of approaches is exclusively consisting of bioinformatic analyses and represents a key downstream analysis for standard next-generation sequencing data sets; see e.g. DePristo et al., (2011) Nature Genetics 43(5):491-8 and references cited therein. Most variant sequence callers are built upon Bayesian algorithms and incorporate the detection probability for a specific variant at a particular position given the known polymorphism rate and sequencing errors. For whole genome and exome sequencing, more sophisticated post-alignment procedures were developed to further increase the accuracy of variant calling. New methods for local realignment around indels, recalibration of base quality scores and adaptive error modeling prior to variant calling allow identifying false-positive variants. Adapting this sequence analysis pipeline and evaluating its performance on sequencing data derived from a single cell genome poses currently the major challenge in single cell genomics. The second category comprises non-computational approaches based on the use of random tag sequences directly coupled to the genomic fragments to be sequenced. These technological developments were primarily focused on the detection of rare variants in heterogeneous cell populations as, for example, frequently found in tumor tissues by deep sequencing. The detection of rare mutations by next-generation sequencing has been described by Schmitt et al. (2012) PNAS 109(36):14508-13 and WO2013/142389. Sequencing accuracy is achieved by the addition of random complementary double-strand DNA adapters to both strands of a double-stranded genomic molecule before amplification. All sequencing reads sharing the same sequencing tag can be merged to a single-strand consensus sequence. In addition, all sequencing reads derived from the complementary strand are identified by the complementary tag sequence allowing creation of a double-strand consensus sequence called Duplex sequence. A real genetic variation is characterized by a perfect match at the same nucleotide in the opposite single-strand consensus.

A further approach called Safe-SeqS was described by Kinde et al. (2011) PNAS 108(23):9530-5. The approach consists of two basic steps. First, the assignment of a unique identifier to each DNA template and, second, the amplification of each uniquely tagged template. Unlike Schmitt et al., Safe-SeqS does not use the information from the complementary strand.

Additional approaches have been published using barcoded adaptors (either ligated via T/A-cloning or blunt end ligation) to identify sample origin. However, none of the approaches comprises an error-correction approach. The first approach uses double-strand DNA adapters that are ligated to blunt ends of double-strand DNA fragments as described in WO 2012/042374. As further described below, these techniques using double-strand adapter molecules are unable to amplify and sequence low amounts of nucleic acid molecules, in particular DNA, in particular the DNA of a single cell or a single DNA molecule.

Similarly, further known approaches comprise the use of partially double-strand DNA adapters, so-called Y-adapters. Such techniques require dA-tailing prior to adapter ligation in order to minimize adapter dimerization. Also, restriction enzyme generated double-strand DNA may be used for Y-adapter ligation, as for example in Monson-Miller et al. (2012) BMC Genomics 13:72. This method involves the use of short barcode sequences (4 bases) for sample identification. However, these techniques are unable to rely on the redundant sequence information contained in the complementary DNA strands for sequencing error identification and/or mutation analysis.

An iterative and regenerative method for DNA sequencing is provided by Jones (1997) BioTechniques 22:938-946 and in U.S. Ser. No. 08/742,755. The method involves restriction enzyme digestion using a type II s restriction enzyme, in particular Fok I or Bse RI. The recognition site is comprised in the adapter sequence. Subsequent to each PCR cycle, the adapter is cleaved from the target DNA, resulting in a loss of the primer binding site for PCR. One cycle of PCR is performed to sequence one base, i.e. significant sample amplification from low amount of DNA is only possible with iterative ligation-amplification cycles. Consequently, the method is not suited for low amounts of DNA.

None of the prior art approaches allows identification of nucleic acid sequences in samples comprising low amounts of DNA or in samples comprising low amounts of nucleic acid molecules, in particular the nucleic acid molecule(s)/DNA of a single cell. In fact, all known approaches as recited herein above are limited to large quantities of DNA. This is inter alia due to the fact that duplex sequencing as described, e.g., in WO2013/142389 uses adaptors for ligation, which are added in large amounts to cellular DNA. The excess of double strand adaptor molecules generates PCR inhibitors. Thus, low amounts of DNA cannot successfully be amplified by using the described approach. Other techniques require information from multiple samples and/or a stochastic-based bioinformatics approach for the identification of mutations and/or sequencing errors. Therefore, there is a need for a sequencing method providing error-free sequence information also from low amounts of input nucleic acid molecules/DNA, in particular the DNA of a single cell.

Thus, the technical problem underlying the present invention is to provide an improved error-free sequencing method of nucleic acid molecules.

The solution to this technical problem is provided by the embodiments as defined herein below and as characterized in the claims.

The invention, accordingly, relates to the following:

A method of error-free sequencing of (a) nucleic acid molecule(s), comprising the steps of:
(a) providing a sample comprising (a) nucleic acid molecule(s);
(b) digesting the nucleic acid molecule(s) with a restriction endonuclease under conditions suitable to obtain nucleic acid molecule fragments of similar length,
wherein said restriction endonuclease is capable of providing 5' overhangs, wherein the terminal nucleotide of the overhang is phosphorylated or,
wherein said restriction endonuclease is capable of providing 3' overhangs, wherein the terminal nucleotide of the overhang is hydroxylated on said nucleic acid molecule fragments;
(c) annealing a first oligonucleotide to said nucleic acid molecule fragments, wherein a first sequence of said first oligonucleotide is complementary to the 5' or 3' overhang, respectively, of said nucleic acid molecule fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence;
(d) ligating said second oligonucleotide to said nucleic acid molecule fragment;
(e) filling in of the generated overhangs;
(f) amplifying said nucleic acid molecule fragments using a third oligonucleotide comprising a sequence binding to said third sequence of said second oligonucleotide; and
(g) sequencing said amplified nucleic acid molecule fragments.

In particular, the present invention relates to the following:

1. A method of error-free sequencing of DNA, comprising the steps of:
   (a) providing a sample comprising DNA;
   (b) digesting the DNA with a restriction endonuclease under conditions suitable to obtain DNA fragments of similar length,
   wherein said restriction endonuclease is capable of providing 5' overhangs, wherein the terminal nucleotide of the overhang is phosphorylated or,
   wherein said restriction endonuclease is capable of providing 3' overhangs, wherein the terminal nucleotide of the overhang is hydroxylated on said DNA fragments;
   (c) annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence;
   (d) ligating said second oligonucleotide to said DNA fragment;
   (e) filling in of the generated overhangs;
   (f) amplifying said DNA fragments using a third oligonucleotide comprising a sequence binding to said third sequence of said second oligonucleotide; and
   (g) sequencing said amplified DNA fragments.

2. The method of item 1, wherein said third oligonucleotide is a primer.

3. The method of item 1, wherein said second oligonucleotide further comprises a fourth sequence comprising a restriction site of a site-specific endonuclease.

4. The method of any one of items 1 to 3, wherein said second oligonucleotide is a DNA oligonucleotide, an RNA oligonucleotide or a DNA/RNA oligonucleotide.

5. The method of item 3, wherein said endonuclease is a homing endonuclease, zinc finger nuclease, TALEN, TFO nuclease or targetron.

6. The method of items 3 or 5, wherein said endonuclease is I-SceI or I-CeuI.

7. The method of any one of items 1 to 6, wherein said method further comprising the step (e'), wherein an exonuclease is added in said step (e').

8. The method of item 7, wherein said exonuclease is an enzyme degrading single-stranded DNA, RNA and/or DNA/RNA molecules.

9. The method of items 7 or 8, wherein said exonuclease is Exonuclease I, mung bean nuclease, Exonuclease T, or RecJ$_f$.

10. The method of any one of items 1 to 9, wherein said DNA comprises (i) the genome or transcriptome of a single cell, (ii) chromosome(s) of a single cell, (iii) nucleic acids from exosomes or other microvesicles of a single cell or (iv) fragment(s) or subfraction(s) of the material of any one of items (i) to (iii).

11. The method of item 10, wherein said single cell is obtained from biological material used in forensics, reproductive medicine, or regenerative medicine.

12. The method of items 10 or 11, wherein said single cell is a tumor cell, a blood cell, a cell from bone marrow aspirates, a cell obtained from a lymph node and/or a cell obtained from microdissected tissue, a blastomere or blastocyst of an embryo, a sperm cell, a cell obtained from amniotic fluid, a cell obtained from blood, or a cell obtained from buccal swabs.

13. The method of item 12, wherein said tumor cell is a disseminated tumor cell, circulating tumor cell or a cell from tumor biopsies.

14. The method of item 12, wherein said blood cell is a peripheral blood cell or a cell obtained from umbilical cord blood.

15. The method of any one of items 1 to 9, wherein said DNA comprises (i) the DNA of more than one single cell, (ii) cell-free fetal DNA of more than one single cell, (iii) cell-free DNA of more than one single cell, in serum and/or plasma of cancer patients or (iv) fragment(s) or subfraction(s) of the material of any one of items (i) to (iii).

16. The method of item 15, wherein said cell-free DNA comprises DNA material from body fluids.
17. The method of any one of items 1 to 16, wherein said method further comprises the step (a'), wherein said DNA is modified by introduction of artificial restriction sites or tags in said step (a').
18. The method of any one of items 1 to 17, wherein said method further comprises the step (a") wherein the DNA is digested with a proteinase in said step (a").
19. The method of item 18, wherein said proteinase is thermo-labil.
20. The method of item 18 or 19, wherein said proteinase is Proteinase K.
21. The method of any one of items 18 to 20, wherein said method further comprises the step (a'''), wherein the proteinase is thermally inactivated in said step (a''').
22. The method of any one of items 1 to 21, wherein said restriction endonuclease used in step (b) recognizes a motif with four to six defined bases.
23. The method of any one of items 1 to 22, wherein said restriction endonuclease used in step (b) recognizes the consensus sequence TTAA.
24. The method of any one of items 1 to 23, wherein said restriction endonuclease used in step (b) is MseI or an isoschizomer thereof.
25. The method of any one of items 1 to 24, wherein said second oligonucleotide is longer than said first oligonucleotide.
26. The method of any one of items 1 to 25, wherein said first oligonucleotide comprises 4 to 15 nucleotides and said second oligonucleotide comprises 30 to 60 nucleotides.
27. The method of any one of items 1 to 26, wherein said randomized sequence comprises 3 to 24 nucleotides.
28. The method of any one of items 1 to 27, wherein said first oligonucleotide comprises the sequence 5'-TAACTGACdd-3' and/or wherein said second oligonucleotide comprises the sequence as shown in SEQ ID NO: 1 and/or wherein said third oligonucleotide comprises the sequence as shown in SEQ ID NO: 2.
29. The method of any one of items 1 to 28, wherein said first oligonucleotide has the sequence 5'-TAACTGACdd-3' and/or wherein said second oligonucleotide has the sequence as shown in SEQ ID NO: 1 and/or wherein said third oligonucleotide has the sequence as shown in SEQ ID NO: 2.
30. The method of any one of items 1 to 29, wherein said method further comprises the step (c'), wherein said first oligonucleotide and said second oligonucleotide are hybridized to each other separately from said DNA fragments and are added to said DNA fragments in said step (c').
31. The method of any one of items 1 to 30, wherein the last 3' nucleotide of the first oligonucleotide is a dd-nucleotide.
32. The method of any one of items 10 to 31, wherein DNA fragments from essentially the whole nuclear genome of said single cell are amplified.
33. The method of any one of items 10 to 32, wherein said single cell has been subjected to chemical fixation.
34. The method of any one of items 3 to 33, wherein said method further comprises the step (f') wherein a homing endonuclease is added in said step (f').
35. The method of item 34, further comprising ligating fragments after restriction by said homing endonuclease.
36. The method of item 35, wherein the ligated fragments are subjected to whole genome sequencing.
37. The method of any one of items 1 to 33, wherein steps (a) to (f) are carried out in one reaction vessel.
38. Use of the sequenced DNA fragments obtained by the method of any one of items 1 to 37 in methods for DNA sequence analysis, generation of cell lineage trees or assessment of copy numbers.
39. The use of item 38, wherein the method for DNA sequence analysis is whole genome sequencing, whole exome sequencing, whole regulome sequencing, sequencing-based methylation analysis, sequencing-based breakpoint detection, ChIP sequencing, or targeted sequencing and variations thereof.
40. A four-part oligonucleotide comprising a fixed sequence, randomized sequence, restriction nuclease recognition site and/or restriction site, and primer binding site, wherein said fixed sequence comprises 4 to 15 nucleotides, said randomized sequence 3 to 24 nucleotides and said restriction nuclease recognition site is a recognition site of a homing endonuclease.
41. The four-part oligonucleotide of item 40, wherein said four-part oligonucleotide is a primer.
42. The four-part oligonucleotide of items 40 or 41, wherein said restriction nuclease recognition site and/or restriction site and said primer binding site are comprised in one sequence.
43. The four-part oligonucleotide of any one of claims 40 to 42, wherein said fixed sequence comprises GTCAGT and/or wherein said restriction nuclease recognition site and/or restriction site comprises SEQ ID NO:3 and/or wherein said primer binding site comprises SEQ ID NO:4.
44. The four-part oligonucleotide of any one of claims 40 to 42, wherein said fixed sequence comprises GTCAGT or wherein said restriction nuclease recognition site or restriction site comprises SEQ ID NO:3 or wherein said primer binding site comprises SEQ ID NO:4.
45. The four-part oligonucleotide of any one of claims 40 to 42, wherein said fixed sequence comprises GTCAGT and wherein said restriction nuclease recognition site or restriction site comprises SEQ ID NO:3 and wherein said primer binding site comprises SEQ ID NO:4.
46. The four-part oligonucleotide of any one of items 39 to 42 comprising SEQ ID NO:14, 5 or 12.

Accordingly, the present invention provides a novel and inventive method of error-free sequencing of DNA. As is evident from the appended examples, the method of error-free sequencing as provided herein comprises in particular error-free DNA analysis comprising prior to error-free DNA analysis a step of DNA sequencing. Low amounts of DNA are preferred as starting material to be employed in the methods of the present invention. In particular, the present invention provides novel and inventive methods of error-free sequencing of DNA of a single cell or a single DNA molecule. The method of error-free sequencing of DNA, in particular low amounts of DNA, provided herein comprises the steps of (a) providing a sample comprising DNA; (b) digesting the DNA with a restriction endonuclease under conditions suitable to obtain DNA fragments of similar length, wherein said restriction endonuclease is capable of providing 5' overhangs, wherein the terminal nucleotide of the overhang is phosphorylated, or, wherein said restriction endonuclease is capable of providing 3' overhangs, wherein the terminal nucleotide of the overhang is hydroxylated on said DNA fragments; (c) annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence; (d) ligating said second oligonucleotide to said DNA fragment; (e) filling in generated overhangs; (f) amplifying said DNA fragments using a third oligonucleotide comprising a sequence binding to said third sequence of said second oligonucleotide; and (g) sequencing said amplified DNA fragments.

In accordance with the invention, the second oligonucleotide may further comprise a fourth sequence, wherein the fourth sequence comprises a restriction site of an endonuclease, preferably a homing endonuclease.

It has been surprisingly found by the inventors that the use of single strand oligonucleotides instead of double strand adaptors avoids the creation of PCR inhibitors and/or self-ligating adaptors, i.e. adaptor molecules that bind to other adaptor molecules and are subject to ligation. To achieve high ligation efficiency of adaptors to low amounts of target DNA addition of adaptor molecules in excess of the amount of target DNA is required. Double strand adaptors will then impede binding of the PCR primer to the target DNA, because the concentration of the complementary sequence is excessively high. This excess of adaptor molecules makes it impossible to use small amounts of target DNA, which cannot be purified from the adaptor-target DNA mix without significant loss of target DNA. In contrast, the present invention provides methods that are independent of the amount of DNA used as starting material. In particular, the methods of the present invention allow error-free sequencing of particularly low amounts of target DNA, which may be as low as the DNA of a single cell and/or a single DNA molecule.

Furthermore, it has surprisingly been found by the inventors that the use of three oligonucleotides allows error-free sequencing independent of the amount of DNA used as starting material. More specifically, methods of the prior art are unable to provide error-free sequencing of, e.g., low amounts of DNA. In contrast, the herein provided methods are designed to amplify and obtain the sequence of any amount of DNA, in particular DNA of a single cell and/or DNA of a single DNA molecule. The herein provided methods may also be used to remove sequencing errors in the amplified and sequenced DNA in order to identify real mutations and correct sequences. This is achieved by the use of three oligonucleotides. In particular, a first oligonucleotide is partially complementary to a generated 3' and/or 5' overhang of a DNA sample that has been fragmented by a restriction endonuclease. When binding to the overhang(s) of the DNA fragments, the first oligonucleotide also generates an overhang, i.e. the first oligonucleotide is longer than the 3' and/or 5' overhang of the DNA fragment. A second oligonucleotide comprising three to four functional parts/sequences comprises a first sequence, herein also named fixed sequence, that is partially complementary to the first oligonucleotide, which enables the second oligonucleotide to bind the overhang generated by the first oligonucleotide, thereby forming a DNA-oligonucleotide-oligonucleotide complex. Accordingly, the first oligonucleotide directs the second oligonucleotide to the target DNA. Use of the first oligonucleotide surprisingly increases the ligation efficiency of the second oligonucleotide to each target DNA fragment. The fixed sequence may be varied, but necessarily comprises a sequence complementary to the first oligonucleotide. After binding of the second oligonucleotide, a single strand ligation is performed that covalently binds the second oligonucleotide to the DNA fragment. The first oligonucleotide is preferably not ligated to the DNA. This may be achieved by synthesizing the oligonucleotide without a 5'-phosphat terminus.

Furthermore, a second sequence of the second oligonucleotide comprises a randomized sequence used as barcode/identifier to uniquely mark each oligonucleotide-DNA complex. The length of the barcode may vary. In particular, the length of the barcode may vary depending on the number of generated DNA fragments. In a further step, the overhang(s) generated by the ligated second oligonucleotide is/are filled in by a polymerase reaction. The second oligonucleotide furthermore comprises a third sequence that is designed to allow a third oligonucleotide to bind. Thus, the third oligonucleotide is complementary to the third sequence of the second oligonucleotide. The third oligonucleotide is designed to allow efficient PCR-based amplification of the entire sample representation, whose sequence is then obtained. Accordingly, the third oligonucleotide serves as primer for PCR amplification.

The term "sequence" refers to sequence information about a nucleic acid molecule or any portion of the nucleic acid molecule that is two or more units (nucleotides) long. The term can also be used as a reference to the nucleic acid molecule itself or a relevant portion thereof.

Nucleic acid molecule sequence information relates to the succession of nucleotide bases in the nucleic acid molecule. For example, if the nucleic acid molecule contains bases Adenine, Guanine, Cytosine, Thymine, or Uracil, or chemical analogs thereof, the nucleic acid molecule sequence can be represented by a corresponding succession of letters A, G, C, T, or U, e.g., a DNA or RNA molecule.

Exemplary, non-limiting methods to be used in order to determine the sequence of a nucleic acid molecule are e.g. methods for sequencing of nucleic acids (e.g. Sanger dideoxy sequencing), massive parallel sequencing methods such as pyrosequencing, reverse dye terminator, proton detection, phospholinked fluorescent nucleotides.

In particular, the resulting PCR products may be subjected to either conventional Sanger-based dideoxy nucleotide sequencing methods or employing novel massive parallel sequencing methods ("next generation sequencing") such as those marketed by Roche (454 technology), Illumina (Solexa technology), ABI (Solid technology) or Pacific Biosciences (SMRT technology). Mutations may be identified from sequence reads by comparison with publicly available sequence data bases or by loss-of-function and/or gain-of-function prediction algorithms implemented in in silico bioinformatic tools such as SIFT and PolyPhen. In particular, mutations may be mutations known in the art as being relevant/decisive for medical indications. Alternatively, mutations may be identified by allele-specific incorporation of molecular tags that can either be detected using enzymatic detection reactions, fluorescence, mass spectrometry or others; see Vogeser (2007) Dtsch Arztebl 104 (31-32), A2194-200.

The term "error-free" sequencing refers to an approach allowing to eliminate to high extend the technical errors introduced during sample processing, e.g. DNA isolation, amplification and/or sequencing. Through the use of randomized barcode/identifiers each discrete allele is labelled at both ends with a unique sequence tag. Sequences flanked by two ligated barcodes can be easily traced as the consensus sequence of two complementary DNA strands can be determined. Lack of complementarity at any nucleotide between the single strand consensus sequences of the same double-stranded DNA fragment should be recognized as technical error. However, the person skilled in the art will readily understand that the term "error-free" does not refer to a complete removal of technical errors, but rather to a reduction of their frequency to a negligible level. In particular, the skilled person will appreciate that when using the DNA of a single cell or a single DNA molecule as starting material to be employed in the methods of the present invention, amplification of the DNA will introduce errors that later can be removed by error correction using the methods of the present invention. Larger amounts of starting material, e.g. DNA extracted from tissue, as also provided herein, may not require DNA amplification prior to DNA sequencing, possibly resulting in a reduced error rate in DNA sequencing, which can also be corrected using the methods of the present invention.

The term "randomized sequence" in accordance with the invention is to be understood as a sequence of nucleotides, wherein each position has an independent and equal probability of being any nucleotide. The random nucleotides can be any of the nucleotides, for example G, A, C, T, U, or chemical analogs thereof, in any order, wherein: G is understood to represent guanylic nucleotides, A adenylic nucleotides, T thymidylic nucleotides, C cytidylic nucleotides and U uracylic nucleotides. The skilled person will appreciate that known oligonucleotide synthesis methods may inherently lead to unequal representation of nucleotides G, A, C, T or U. For example, synthesis may lead to an overrepresentation of nucleotides, such as G in randomized DNA sequences. This may lead to a reduced number of unique random sequences as expected based on an equal representation of nucleotides. However, the skilled person is well aware that the overall number of unique random sequences comprised in the second oligonucleotide used in the methods of the invention will generally be sufficient to clearly identify each target DNA fragment. This is because the skilled person will also be aware of the fact that the length of the randomized sequence may be varied depending on the number of fragments resulting from DNA fragmentation. The expected number of DNA fragments may be derived from the number of cleavage sites of a restriction endonuclease and the length of the target DNA. Accordingly, the potential unequal representation of nucleotides in the randomized sequence of the second oligonucleotide used in the methods of the invention, which is due to unequal coupling efficiencies of nucleotides in known standard oligonucleotide synthesis methods, can easily be taken into account by the skilled person based on the general knowledge in the art. In particular, the skilled person is well aware that the length of the randomized sequence may be increased in order to obtain an increased number of unique randomized sequences.

The terms "complementary" or "complementarity" refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some nucleotides of the nucleic acids bind to each other, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands. As used in accordance with the present invention, the term "DNA fragments of similar length" denotes fragments, which, at a statistical level, have a size which is of comparable length. DNA fragments of comparable length are, for example, fragments from about 50+/−5 bp to about 4 kbp+/−0.4 kbp. The length range of DNA fragments that is preferably generated is advantageously between about 50 bp and about 4 kbp. DNA fragments of greater or shorter length may be used as well, although they may be amplified or represented to a lesser extent than the fragments of the size range defined above. DNA fragments are preferably suitable for linear and/or exponential amplification. Preferably, the DNA fragments have a size of <3 kbp, more preferably said DNA fragments have an average length of about 1000 bp and particularly preferred are fragments of about 100-400 bp.

The terms "5' overhangs" and "3' overhangs" as used herein means the 5' phosphate group or 3' hydroxyl group, provided e.g. by a staggered cleavage of DNA by restriction endonucleases, and denotes a single stranded overhanging 5' end on DNA or a single stranded overhanging 3' end on DNA, respectively.

The term "amplifying" refers to repeated copying of a specified sequence of nucleotides resulting in an increase in the amount of said specified sequence of nucleotides and allows the generation of a multitude of identical or essentially identical (i.e. at least 95%, more preferred at least 98%, even more preferred at least 99% and most preferred at least 99.5% such as 99.9% identical) nucleic acid molecules or parts thereof. Such methods are well established in the art; see Sambrook et al. "Molecular Cloning, A Laboratory Manual", $2^{nd}$ edition 1989, CSH Press, Cold Spring Harbor. Various amplification methods may be applied, these are for example, rolling circle amplification (such as in Liu, et al., "Rolling circle DNA synthesis: Small circular oligonucleotides as efficient templates for DNA polymerases," J. Am. Chem. Soc. 118:1587-1594 (1996)), isothermal amplification (such as in Walker, et al., "Strand displacement amplification—an isothermal, in vitro DNA amplification technique", Nucleic Acids Res. 20(7):1691-6 (1992)), ligase chain reaction (such as in Landegren, et al., "A Ligase-Mediated Gene Detection Technique," Science 241:1077-1080, 1988, or, in Wiedmann, et al., "Ligase Chain Reaction (LCR)—Overview and Applications", PCR Methods and Applications (Cold Spring Harbor Laboratory Press, Cold Spring Harbor Laboratory, N Y, 1994) pp. S51-S64.). Polymerase chain reaction amplification is, however, preferred. They include polymerase chain reaction (PCR) and modifications thereof, ligase chain reaction (LCR) to name some preferred amplification methods.

The terms "anneal" or "hybridize" and "annealing" or "hybridization" refer to the formation of complexes between nucleotide sequences that are sufficiently complementary to form complexes via Watson-Crick base pairing. With respect to the present invention, nucleic acid sequences that are "complementary to" or "complementary with" or that "hybridize" or "anneal" to or with each other should be capable of forming or form "hybrids" or "complexes" that are sufficiently stable to serve the intended purpose. Hybridization or annealing and the strength of hybridization (i.e., the strength of the association between nucleic acid strands) is influenced by many factors well known in the art including e.g. the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol or betaine), the molarity of the hybridizing strands and the G:C content of the nucleic acid strands.

The methods of the present invention allow error-free sequencing of DNA. It is well known in the art that amplification and/or sequencing introduce errors to the final sequencing result. This is due to, inter alia, the natural error rate of the used polymerase and/or ambiguities of the identity of the base during sequencing. The best way to identify errors is to use the redundant sequence information of a double strand DNA molecule. This is because the probability of the introduction of errors during amplification and/or sequencing at the same position of a DNA sample is minimal. The herein provided methods allow the identification of such errors by making use of the redundant sequence information of a double stranded DNA molecule by adding a unique identifier/barcode to each single strand DNA molecule/fragment. Accordingly, each double stranded DNA molecule/fragment is tagged with a unique identifier/barcode on either both 5' ends or both 3' ends, respectively. The subsequent fill-in reaction leads to the generation of single strand DNA molecules that are tagged on each site of the target DNA with two distinct barcodes. More specifically, each single stranded target DNA molecule is tagged with the barcode of the second oligonucleotide that was ligated to the target DNA fragment and the complementary sequence of the barcode of the second oligonucleotide that was ligated to the complementary strand of the target DNA fragment. Accordingly, both single strand DNA molecules of a double strand DNA fragment can be unambiguously identified based on both barcode sequences that are attached to the 5' and 3' end, respectively, of each single strand DNA. In a first step, the sequences are sorted according to the barcodes at the 3' and 5' ends. In a second step the complementary strand of the original double-stranded DNA molecule is identified via the complementary barcodes. Thereby it is possible to identify inter alia errors that have been introduced during sample preparation, such as amplification and/or sequencing and thus to identify true mutations in, e.g., alleles of tumour cells. The reliable identification of true mutations in tumour cells of individual patients may enable to develop and/or improve efficient personalized targeted cancer therapies. In addition to the identification of mutations in a DNA molecule, the methods of the present invention may be used for error-free identification of modifications of the target DNA molecule, e.g. methylation, in particular methylation of cytosines (Laird 2010 Nature Reviews Genetics 11, 191-203).

Oligonucleotides of the invention may be DNA oligonucleotides, RNA oligonucleotides or DNA/RNA oligonucleotides. In particular, the oligonucleotides may be partially or completely comprised of ribonucleic acid nucleotides and/or deoxyribonucleic acid nucleotides, respectively. In one embodiment of the invention, the second sequence of the second oligonucleotide consists of ribonucleic acid nucleotides. Accordingly, after ligating the second oligonucleotide of DNA-RNA-DNA composition to a single strand molecule of a double-stranded DNA-fragment, the addition of enzyme(s) with RNA-dependent and/or DNA-dependent DNA synthesis properties will generate double-stranded DNA fragments of the composition DNA:DNA-RNA:DNA-DNA:DNA at the site of the ligated second oligonucleotide. The addition of ribonuclease(s) specifically hydrolyzing phosphodiester bonds in RNA-DNA hybrids and digesting the single-stranded RNA part of free second oligonucleotides will remove all RNA sequences in the reaction thereby creating a double-stranded fragment with an internal gap at the site of the second oligonucleotide and the third oligonucleotide. The resulting gap in the double-stranded DNA-fragment will be filled by the DNA polymerase already present in the reaction. The addition of a ligase will covalently link the extended part of the second oligonucleotide to the fixed sequence of the second oligonucleotide.

The second oligonucleotide of the invention may furthermore comprise a fourth sequence that may contain a site-specific motive for a restriction enzyme, for example of a homing endonuclease. The fourth sequence is thereby preferred to be located either between the second and third sequence or within the third sequence. Accordingly, the presence of the fourth sequence of the second oligonucleotide allows reducing the length of the amplification product by removing of the oligonucleotide binding site, i.e. the third sequence, which is not required for DNA sequencing. This allows sequencing of longer cell or sample-derived DNA fragments due to the shortening of the amplification product. The restriction enzyme site can be used to ligate sequencing adaptors with high efficiency or to concatenate the DNA fragments after amplification for next generation sequencing technologies such as whole genome sequencing approaches.

As used herein, the term "restriction endonuclease" refers to enzymes capable of cutting double stranded DNA at or near a specific nucleotide sequence. Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites remote from the recognition site and have distinct binding and cleavage units. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al., *Proc. Natl. Acad. Sci. USA,* 89:4275-4279, 1992; Li et al., *Proc. Natl. Acad. Sci. USA,* 90:2764-2768, 1993; Kim et al., *J. Biol. Chem.,* 269:31,978-31,982, 1994b; Kim et al., *Proc. Natl. Acad. Sci. USA,* 91:883-887, 1994a.

Exemplary Type IIS restriction enzymes are described in International Publication WO 07/014,275, incorporated herein in its entirety. Other restriction enzymes also contain separable binding and cleavage domains, and these are contemplated by the present disclosure. See, for example, Roberts et al., *Nucleic Acids Res.,* 31:418-420, 2003.

Any nuclease having a target site in the target DNA can be used in the methods disclosed herein. For example, homing endonucleases and meganucleases have very long recognition sequences, some of which are likely to be present, on a statistical basis, once in a human-sized genome.

Exemplary homing endonucleases suitable for use in step (f) of the methods of the invention include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al., *Nucleic Acids Res.,* 25:3379-3388, 1997; Dijon et al., *Gene,* 82:115-118, 1989; Perler et al., *Nucleic Acids Res.,* 22:1125-1127, 1994; Jasin, *Trends Genet.,* 12:224-228, 1996; Gimble et al., *J. Mol. Biol.,* 263:163-180, 1996; Argast et al., *J. Mol. Biol.,* 280: 345-353, 1998 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al., *Molec. Cell,* 10:895-905, 2002; Epinat et al., *Nucleic Acids Res.,* 31:2952-2962, 2003; Ashworth et al., *Nature,* 441:656-659, 2006; Paques et al., *Current Gene Therapy,* 7:49-66, 2007.

Furthermore, the present invention provides for a four-part oligonucleotide, comprising a first, second, third and fourth sequence, wherein the first sequence comprises a fixed sequence, the second sequence comprises a randomized sequence, the third sequence comprises a primer binding site and the fourth sequence comprises a restriction nuclease recognition site and/or restriction site. In accordance with the present invention, the fixed sequence preferably comprises about 4 to 15 nucleotides, the randomized sequence preferably comprises about 3 to 24 nucleotides and the restriction nuclease recognition site preferably comprises a recognition site of a homing endonuclease. The four-part oligonucleotide has the following preferred 5' to 3' order of the four sequences/parts: 5' end followed by primer binding site (third sequence) or restriction site (fourth sequence) followed by primer binding site or restriction site (depending on selection of most 5' sequence) followed by random sequence (second sequence) followed by fixed sequence (first sequence) followed by 3' end.

The term "oligonucleotide", in accordance with the present invention, includes any nucleic acid molecule, such as DNA, e.g. cDNA or genomic DNA, and RNA. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see Braasch and Corey, Chem Biol 2001, 8: 1), etc. LNA is an RNA derivative in which the ribose ring is constrained by a methylene linkage between the 2'-oxygen and the 4'-carbon. They may contain additional non-natural or derivative nucleotide bases, as will be readily appreciated by those skilled in the art.

Furthermore, the present invention relates to an oligonucleotide capable of specifically amplifying the nucleic acid molecules of the present invention. Accordingly, oligonucleotides within the meaning of the invention may be capable of serving as a starting point for amplification, i.e. may be capable of serving as primers. In particular, the third oligonucleotide of the invention preferably serves as primer for PCR amplification. Said oligonucleotide may also comprise oligoribo- or desoxyribonucleotides which are complementary to a region of one of the strands of a nucleic acid molecule. According to the present invention, a person skilled in the art would readily understand that the term "primer" may also refer to a pair of primers that are with respect to a complementary region of a nucleic acid molecule directed in the opposite direction towards each other to enable, for example, amplification by polymerase chain reaction (PCR). Purification of the primer(s) is generally envisaged, prior to its/their use in the method of the present invention. Such purification steps can comprise HPLC (high performance liquid chromatography) or PAGE (polyacrylamide gel-electrophoresis), and are known to the person skilled in the art.

When used in the context of primers, in particular the third oligonucleotide of the invention, the term "specifically" means that only the desired nucleic acid molecules as described herein are amplified. Thus, a primer according to the invention is preferably a primer, which binds to a region of a nucleic acid molecule which is unique for this molecule. In connection with a pair of primers, according to the invention, it is possible that one of the primers of the pair is specific in the above described meaning or both of the primers of the pair are specific.

The 3'-OH end of a primer is used by a polymerase to be extended by successive incorporation of nucleotides. The primer or pair of primers of the present invention can be used, for example, in primer extension experiments on template DNA according to methods known by the person skilled in the art. Preferably, the primer or pair of primers of the present invention are used for amplification reactions on template DNA, preferably genomic DNA. The term "template DNA" refers to DNA molecules or fragments thereof of any source or nucleotide composition, that comprise a target nucleotide sequence as defined above. The primer or pair of primers can also be used for hybridization experiments as known in the art. Preferably, the primer or pair of primers are used in polymerase chain reactions to amplify sequences corresponding to a sequence of the nucleic acid molecule of the present invention. It is known that the length of a primer results from different parameters (Gillam, Gene 8 (1979), 81-97; Innis, PCR Protocols: A guide to methods and applications, Academic Press, San Diego, USA (1990)). Preferably, the primer should only hybridize or bind to a specific region of a target nucleotide sequence. The length of a primer that statistically hybridizes only to one region of a target nucleotide sequence can be calculated by the following formula: $(¼)^x$ (whereby x is the length of the primer). However, it is known that a primer exactly matching to a complementary template strand must be at least 9 base pairs in length, otherwise no stable-double strand can be generated (Goulian, Biochemistry 12 (1973), 2893-2901). It is also envisaged that computer-based algorithms can be used to design primers capable of amplifying DNA. It is also envisaged that the primer or pair of primers is labeled. The label may, for example, be a radioactive label, such as $^{32}$P, $^{33}$P or $^{35}$S. In a preferred embodiment of the invention, the label is a non-radioactive label, for example, digoxigenin, biotin and fluorescence dye or dyes.

The term "filling in" or "fill-in" as used herein means a DNA synthesis reaction, initiated at 3' hydroxyl ends, leading to a fill in of the complementary strand. This DNA synthesis reaction is preferably carried out in the presence of dNTPs (dATP, dGTP, dCTP and dTTP, dUTP, and/or chemical analogs thereof). Thermostable DNA polymerases such as Taq polymerases are frequently used and are well known to the person skilled in the art.

In a preferred embodiment of the present invention, the fourth sequence of the second oligonucleotide of the invention comprises a restriction site of a site-specific endonuclease. In this regard, restriction sites of rarely cutting endonucleases are preferred. More specifically, restriction sites of native or engineered synthetic endonucleases or native or engineered enzymes typically cutting human genomic DNA very infrequently or enabling site-directed cleavage of nucleic acid sequences infrequently present in the human genome are preferred. The engineered restriction enzymes may be capable of site-specifically recognizing sequences, which are not present in the human genome, but which have been introduced artificially. The endonuclease may be a homing endonuclease, zinc finger endonuclease, TALEN, TFO nuclease or targetron. It is preferred that the endonuclease is I-SceI or I-CeuI. It is therefore preferred that the restriction site recognized by the endonuclease is 5'-TAGGGATAACAGGGTAAT-3' (SEQ ID NO: 3) or 5'-TAACTATAACGGTCCTAAGGTAGCGAA-3' (SEQ ID NO: 11) when using I-SceI or I-CeuI, respectively.

The site-specific endonuclease may be added prior to step (g) of the methods of the invention, i.e. prior to sequencing the amplified nucleic acid molecules, preferably the DNA. It is preferred that the site-specific endonuclease is added in a step (f'), after step (f). Accordingly, it is preferred that the methods of the invention further comprise the step (f'), wherein a site-specific endonuclease, in particular a homing endonuclease, is added in step (f'). It is preferred that the site-specific endonuclease is a homing endonuclease, more preferably either I-SceI or I-CeuI.

Methods of the present invention may further comprise the addition of an exonuclease. Since exonucleases do not have specific recognition sites, after the fill-in reaction, the target DNA with the added artificial sequences will consist of double stranded DNA that cannot be digested by single-strand specific exonucleases. Therefore, single-strand specific exonuclease will affect only unligated oligonucleotide sequences. In particular, the exonuclease may be added in order to degrade excess single stranded nucleic acid molecules, e.g. DNA and/or RNA, preferably DNA. Specifically, the exonuclease may be added in order to degrade the first and excess second oligonucleotide used in the methods of the invention prior to amplification. Thus, it is preferred that the exonuclease is added prior to step (f) of the methods of the present invention. More specifically, it is preferred that the methods of the invention further comprise a step (e'), wherein an exonuclease is added in step (e'). The addition of an exonuclease avoids unwanted side products during amplification. Preferably, the exonuclease degrades single-stranded nucleic acid molecules in the 5' to 3' direction whilst not acting on any other nucleic acid molecule or degrades single-stranded nucleic acid molecules in the 3' to 5' direction whilst not acting on any other nucleic acid molecule. It is preferred that the restriction site recognized by the exonuclease is that of Exonuclease I, mung bean nuclease, Exonuclease T, or RecJ$_f$. It is most preferred that the removal of nucleotides from single-stranded DNA molecules is catalyzed by Exonuclease I or RecJf.

While any DNA sample may be used for the methods of the present invention, it is preferred that the used DNA sample comprises (i) the genome or transcriptome of a single cell, (ii) chromosome(s) of a single cell, (iii) nucleic acids from exosomes or other microvesicles of a single cell or (iv) fragment(s) or subfraction(s) of the material of any one of items (i) to (iii).

The single cell used in the methods of the present invention may be obtained from biological material used in forensics, reproductive medicine or regenerative medicine. Accordingly, the single cell may be a tumor cell, a blood cell, a cell from bone marrow aspirates, a cell from a lymph node and/or a cell obtained from a microdissected tissue, a blastomere or blastocyst of an embryo, a sperm cell, a cell obtained from amniotic fluid, or a cell obtained from buccal swabs. It is preferred that the tumor cell is a disseminated tumor cell, circulating tumor cell or a cell from tumor biopsies. It is furthermore preferred that the blood cell is a peripheral blood cell or a cell obtained from umbilical cord blood. It is particularly preferred that the DNA sample consists of (i) the genome or transcriptome of a single cell, (ii) chromosome(s) of a single cell, (iii) nucleic acids from exosomes or other microvesicles of a single cell or (iv) fragment(s) or subfraction(s) of the material of any one of items (i) to (iii).

In another aspect of the invention, the DNA sample may also comprise (i) the DNA of more than one single cell, (ii) cell-free fetal DNA of more than one single cell, (iii) cell-free DNA of more than one single cell in serum and/or plasma (iv) fragment(s) or subfraction(s) of the material of any one of items (i) to (iii). The DNA sample may also consist of the DNA of more than one single cell, cell-free fetal DNA of more than a single cell, or cell-free DNA of more than a single cell in serum and/or plasma of cancer patients. The DNA sample may be obtained from more than one single cell, in particular two or more. The DNA sample is preferred to be obtained from 2 to 5000 single cells.

Furthermore, the DNA used in the methods of the present invention may be modified. In particular, the DNA used for the methods of the present invention may be modified by introduction of artificial restriction sites or tags. It is preferred that the modification to the DNA used in the methods of the present invention takes place prior to amplifying the DNA. In particular, it is preferred that the methods of the invention further comprise a step (a'), wherein the DNA is modified by introduction of artificial restriction sites and/or tags in step (a').

The single cell and/or the more than a single cell used in the methods of the present invention may be of any origin. They/it may be obtained from various sources of biological material. The biological material used as origin of the single cell(s) may, e.g., be used in forensics, reproductive medicine or regenerative medicine. It is preferred that the single cell or the single cells used in the methods of the invention, is/are disseminated tumor cell(s), circulating tumor cell(s), peripheral blood cell(s), cell(s) from bone marrow aspirates, cell(s) from tumor biopsies, cell(s) obtained from umbilical cord blood, cell(s) obtained from a lymph node and/or cell(s) obtained from microdissected tissue, blastomere(s) or blastocyst(s) of an embryo, sperm cell(s), cell(s) obtained from amniotic fluid, or cell(s) obtained from buccal swabs, or polar bodies.

The methods of the present invention may further comprise, prior to step (b), in particular after step (a), the step (a''), wherein said sample comprising DNA is digested with a proteinase. The proteinase may be thermo-labil or inactivated by other means such as chemical inactivation. Preferably, said proteinase is thermo-labil. Accordingly, said proteinase can be thermally inactivated in step (a'''). It is particularly preferred that said proteinase is Proteinase K.

The methods of the present invention may also comprise a step of DNA methylation analysis. It is known that epigenetic mechanisms play important roles during normal development, aging and a variety of disease conditions. Such diseases may be human diseases, including cancer, multiple sclerosis, diabetes, and/or schizophrenia. Hypermethylation of CpG islands located in the promoter regions of tumor suppressor genes is firmly established as a frequent mechanism for gene inactivation in cancers (Hansen et al. 2011. Nat. Genet. 43, 768-775). Methylation of the 5' carbon of cytosine is a form of epigenetic modification that does not affect the primary DNA sequence, but affects secondary interactions that play a critical role in the regulation of gene expression. Aberrant DNA methylation may suppress transcription and subsequently gene expression. Methylation analysis as in the methods of the present invention may comprise selective modification of the target DNA. Such modification may comprise the addition of methylation-dependent restriction enzymes (MDREs) or methylation-sensitive restriction enzymes (MSREs), preferably MDREs. Selective modification of the target DNA may also comprise addition of a chemical agent that is able to selectively differentiate between methylated or unmethylated nucleotides. In particular, methylation analysis as in the present invention is able to selectively identify methylated cytosines that may later be read-out using the error-free sequencing method of the present invention. For example, treatment with bisulfite is known to convert unmethylated cytosines (C) to uracil (U) while methylated cytosines are not converted (Frommer et al. 1992. Proc. Natl. Acad. Sci. USA 89, 1827-1831). Sequencing of DNA subsequent to treatment with bisulfite may be used to identify methylated nucleotides, in particular cytosines. Treatment with MDREs leads to methylation-dependent restriction of DNA fragments, while treatment with MSREs leads to methylation-dependent inhibition of restriction. Sequencing of DNA subsequent to MDRE/MSRE restriction in addition to MseI restriction may be used to identify methylated nucleotides, in particular cytosines. Accordingly, the present invention provides a method of error-free DNA methylation analysis comprising as a further step to the methods of the present invention a step of selectively modifying the target DNA, in particular a step of differentiating between methylated and unmethylated nucleotides comprised in the target DNA. In one embodiment, the present invention provides an error-free method of DNA methylation analysis comprising prior to step (g) of the methods of the invention a step of treating the DNA with bisulfite. Accordingly, the present invention provides a method comprising the steps of:

(a) providing a sample comprising DNA;
(b) adding an agent to said DNA that selectively modifies methylated nucleic acid residues, in particular bisulfite;
(c) digesting the DNA with a restriction endonuclease under conditions suitable to obtain DNA fragments of similar length,
    wherein said restriction endonuclease is capable of providing 5' overhangs, wherein the terminal nucleotide of the overhang is phosphorylated or,
    wherein said restriction endonuclease is capable of providing 3' overhangs, wherein the terminal nucleotide of the overhang is hydroxylated on said DNA fragments;
(d) annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence;
(e) ligating said second oligonucleotide to said DNA fragment;
(f) filling in of the generated overhangs;
(g) amplifying said DNA fragments using a third oligonucleotide comprising a sequence binding to said third sequence of said second oligonucleotide;
(h) sequencing said amplified DNA fragments; and
(i) identifying methylated nucleic acid residues, wherein when bisulfite is used as agent in step (b), a cytosine (C) corresponds to a methylated residue in said DNA sample and an uracil (U) corresponds to an unmethylated residue in said DNA sample.

It is preferred that the error-free method of DNA preparation with subsequent DNA sequence analysis also comprises methylation analysis that comprises the addition of a methylation-dependent restriction enzyme (MDRE) or methylation-sensitive restriction enzyme (MSRE), preferably a MDRE, to selectively differentiate between methylated and unmethylated nucleotides comprised in the target DNA. It is furthermore preferred that the MDRE or MSRE, preferably MDRE, is added prior to amplifying the target DNA fragment, i.e. prior to step (f) of the methods of the invention. Preferably, the MDRE or MSRE is added subsequent to ligating the second oligonucleotide of the invention to the DNA fragments, i.e. subsequent to step (d) of the methods of the invention. However, it is also contemplated that the MDRE or MSRE is added together with or prior to digesting the DNA with a restriction endonuclease, i.e. step (b) of the methods of the invention.

Subsequent to addition of the MDRE or MSRE, preferably MDRE, the generated DNA fragments are ligated with the second oligonucleotide of the present invention in order to uniquely identify each DNA fragment and allow error-free DNA analysis as provided herein. Examples of MDRE(s) and MSRE(s) preferred for use in the methods of the present invention are, inter alia, FspEI, MspJI, LpnPI and AccII, HpaII, DpnI, respectively.

Accordingly, the present invention provides a method comprising the following steps:

(a) providing a sample comprising DNA;
(b) digesting the DNA with a restriction endonuclease under conditions suitable to obtain DNA fragments of similar length,
    wherein said restriction endonuclease is capable of providing 5' overhangs, wherein the terminal nucleotide of the overhang is phosphorylated or,
    wherein said restriction endonuclease is capable of providing 3' overhangs, wherein the terminal nucleotide of the overhang is hydroxylated on said DNA fragments;
(c) annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence;
(d) ligating said second oligonucleotide to said DNA fragment;
(e) digesting said ligated DNA fragments with a MDRE or MSRE, preferably a MDRE;
(f) annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence;
(g) ligating said second oligonucleotide to said DNA fragment;
(h) filling in of the generated overhangs;
(i) amplifying said DNA fragments using a third oligonucleotide comprising a sequence binding to said third sequence of said second oligonucleotide; and
(j) sequencing said amplified DNA fragments.

It is particularly preferred that the restriction endonuclease used in accordance with the present invention, in particular used in the methods of the invention in step (b), recognizes a motif with four to six defined bases. Such endonucleases comprise enzymes which have four distinct nucleotides, e.g. MseI, in their recognition site as well as enzymes where an additional wobble base/s lie/s within the restriction site, like e.g. ApoI. Preferably, the restriction endonuclease used in accordance with the present invention, in particular used in the methods of the invention in step (b), recognizes the consensus sequence TTAA.

It is most preferred for the methods of the present invention, in particular for step (b) of the methods of the invention that the restriction endonuclease is MseI or an isoschizomer thereof.

It is furthermore preferred that the restriction endonuclease used in step (b) of the methods of the invention is not a restriction endonuclease capable of cleaving DNA at sites remote from the recognition site. For example, the type IIS enzyme Fok I catalyzes double-stranded cleavage of DNA, at 9 nucleotides from its recognition site on one strand and 13 nucleotides from its recognition site on the other. Accordingly, it is preferred that the restriction endonuclease used in step (b) of the methods of the invention is not a type IIS restriction endonuclease.

In a further aspect of the present invention, the second oligonucleotide used in the methods of the present invention is longer than the first oligonucleotide. The excess length of the second oligonucleotide with respect to the first oligonucleotide regulates binding/hybridization of the second oligonucleotide to the first oligonucleotide, in particular of the first sequence of the second oligonucleotide, i.e. the fixed sequence, to the second sequence of the first oligonucleotide. Also, it is preferred that the first oligonucleotide dissociates from the oligonucleotide-DNA complex after the second oligonucleotide is ligated to the DNA fragment. Accordingly, it is preferred that binding/hybridization is optimized to allow specific binding of the second sequence of the first oligonucleotide to the first sequence, i.e. fixed sequence, of the second oligonucleotide and that binding/hybridization is optimized to allow dissociation of the first oligonucleotide from the oligonucleotide-DNA complex. Preferably, the first oligonucleotide comprises about 4 to 15 nucleotides and the second oligonucleotide comprises about 30 to 60 nucleotides.

The length of the randomized sequence, i.e. the second sequence of the second oligonucleotide, depends on the desired number of unique barcodes/identifiers and may be varied accordingly. Furthermore, it is preferred that the second sequence of the second oligonucleotide used in the methods of the present invention, i.e. the randomized sequence of the second oligonucleotide, comprises about 3 to 24 nucleotides. It is more preferred that the second sequence of the second oligonucleotide used in the methods of the present invention, i.e. the randomized sequence of the second oligonucleotide, comprises at least 3, more preferred at least 4 and most preferred at least 5 nucleotides.

In accordance with the present invention, the first oligonucleotide comprises a first sequence complementary to the generated overhang of the DNA fragment(s), preferably comprising the nucleotides T and A, a second sequence complementary to the fixed sequence of the second oligonucleotide, which is varied from each sample to be analyzed and which preferably comprises 4 to 15 nucleotides, and a nucleotide without a 5'-phosphat terminus, preferably the nucleotide C.

The variation of the fixed sequence of the second oligonucleotide and accordingly the variation of the second sequence of the first oligonucleotide, allows the distinct identification of samples based on the fixed sequence that may be associated with each sample as sample identifier (SID). This enables unequivocal identification of sequence reads of a particular sample within a multitude of reads originating from other specimens, allowing parallel analysis of multiple samples within one sequencing run. Accordingly, this allows for a higher sample throughput as more independently amplified samples can be processed simultaneously for sequencing. In addition, the SID can be used to parse sequencing files thereby allocating sequences clearly to one sample. Pre-sorted sequences will enable a more rapid assessment of the patient samples.

In one particular embodiment of the invention, it is preferred that the first oligonucleotide used in the methods of the present invention comprises a sequence at least 50%, 55%, 60%, 65%, 70%, 75%, 80%, 85%, preferably 90%, 95% or, most preferably, 100% identical to the sequence 5'-TAACTGACdd-3' and/or the second oligonucleotide used in the methods of the present invention comprises a sequence at least 50%, 55%, 60%, 65%, 70%, 75%, 80%, 85%, preferably 90%, 95% or, most preferably, 100% identical to the sequence as shown in SEQ ID NO: 1 and/or the third oligonucleotide used in the methods of the present invention comprises a sequence at least 50%, 55%, 60%, 65%, 70%, 75%, 80%, 85%, preferably 90%, 95% or, most preferably, 100% identical to the sequence as shown in SEQ ID NO: 2.

In a further embodiment of the invention, it is preferred that the first oligonucleotide used in the methods of the present invention comprises a sequence at least 50%, 55%, 60%, 65%, 70%, 75%, 80%, 85%, preferably 90%, 95% or, most preferably, 100% identical to the sequence 5'-TAACGACdd-3' and/or the second oligonucleotide used in the methods of the present invention comprises a sequence at least 50%, 55%, 60%, 65%, 70%, 75%, 80%, 85%, preferably 90%, 95% or, most preferably, 100% identical to the sequence as shown in SEQ ID NO: 6 and/or the third oligonucleotide used in the methods of the present invention comprises a sequence at least 50%, 55%, 60%, 65%, 70%, 75%, 80%, 85%, preferably 90%, 95% or, most preferably, 100% identical to the sequence as shown in SEQ ID NO: 2.

It is most preferred that the first oligonucleotide used in the methods of the invention has the sequence 5'-TAACTGACdd-3' and/or the second oligonucleotide used in the methods of the invention has a sequence as shown in SEQ ID NO: 1 and/or the third oligonucleotide used in the methods of the invention has a sequence as shown in SEQ ID NO: 2.

In a further aspect of the invention, the first and second oligonucleotide used in the methods of the present invention may be hybridized to each other separately from the DNA. In particular, the hybridized oligonucleotides may be added to the DNA or DNA fragments prior to step (d) of the methods of the invention, i.e. prior to ligation, in particular after step (c) of the methods of the invention. Accordingly, it is preferred that the methods of the invention further comprise a step (c'), wherein the first oligonucleotide and second oligonucleotide are hybridized to each other separately from the DNA fragments and are added to the DNA fragments in step (c').

The first oligonucleotide used in the methods of the present invention can be additionally modified in that the last 3' nucleotide of said oligonucleotide is a dideoxy (dd)-nucleotide.

The methods of the invention allow amplification and/or error-free DNA analysis of essentially the whole nuclear genome of a cell, preferably amplification of essentially the whole genome of a single cell. As it is understood by a person skilled in the art, whole genome amplification refers to methods wherein essentially the whole genome is amplified, not necessarily referring to an amplification method wherein each nucleotide present in the genome is amplified. However, it is preferred that the methods of the present invention amplify the whole genome of a cell, preferably the whole genome of a single cell.

The single cell used in the methods of the present invention may have been subjected to chemical fixation. The chemical fixation may comprise fixation using formalin and/or aceton.

In accordance with the invention, a homing endonuclease may be added prior to step (g) of the methods of the invention, in particular after step (f) of the methods of the invention. Accordingly, it is preferred that the methods of the invention further comprise a step (f'), wherein a homing endonuclease is added in step (f'). In this regard, it is preferred that said homing endonuclease is I-SceI or I-CeuI.

Methods of the present invention may be carried out in one reaction vessel. In particular, steps (a) to (f) of the methods of the present invention may be carried out in one reaction vessel. However, it is preferred that the site-specific endonuclease reaction (step f'), preferably homing endonuclease reaction, is carried out in a separate reaction vessel.

In a preferred embodiment of the present invention, the method of error-free sequencing of DNA comprises the steps of (a) providing a sample comprising DNA of a single cell; (b) digesting the DNA with a restriction endonuclease under conditions suitable to obtain DNA fragments of similar length, wherein said restriction endonuclease is capable of providing 5' overhangs wherein the terminal nucleotide of the overhang is phosphorylated or 3' overhangs wherein the terminal nucleotide of the overhang is hydroxylated on said DNA fragments and wherein said restriction endonuclease recognizes the consensus sequence TTAA; (c) annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence; (d) ligating said second oligonucleotide to said DNA fragment; (e) filling in of generated overhangs; (f) amplifying said DNA fragments using a third oligonucleotide comprising a first sequence binding to said third sequence of said second oligonucleotide; and (g) sequencing said amplified DNA fragments.

In one embodiment of the present invention, the method of error-free sequencing of DNA comprises the steps of (a) providing a sample comprising DNA; (b) digesting the DNA with a restriction endonuclease under conditions suitable to obtain DNA fragments of similar length, wherein said restriction endonuclease is capable of providing 5' overhangs wherein the terminal nucleotide of the overhang is phosphorylated or 3' overhangs wherein the terminal nucleotide of the overhang is hydroxylated on said DNA fragments and wherein said restriction endonuclease recognizes the consensus sequence TTAA; (c) annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence, wherein said first oligonucleotide comprises the nucleic acid sequence 5'-TAACTGACdd-3' and wherein said second oligonucleotide comprises a nucleic acid sequence as set forth in SEQ ID NO:1; (d) ligating said second oligonucleotide to said DNA fragment; (e) filling in of generated overhangs; (f) amplifying said DNA fragments using a third oligonucleotide comprising a first sequence binding to said third sequence of said second oligonucleotide, wherein said third oligonucleotide comprises a nucleic acid sequence as set forth in SEQ ID NO:2; and (g) sequencing said amplified DNA fragments.

In another embodiment of the present invention the method of error-free sequencing of DNA comprises the steps of (a) providing a sample comprising DNA; (b) digesting the DNA with a restriction endonuclease under conditions suitable to obtain DNA fragments of similar length, wherein said restriction endonuclease is capable of providing 5' overhangs wherein the terminal nucleotide of the overhang is phosphorylated or 3' overhangs wherein the terminal nucleotide of the overhang is hydroxylated on said DNA fragments and wherein said restriction endonuclease is MseI or an isoschizomer thereof; (c) annealing of the first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence, wherein said first oligonucleotide has the nucleic acid sequence 5'-TAACTGACdd-3' and wherein said second oligonucleotide has a nucleic acid sequence as set forth in SEQ ID NO:1; (d) ligating said second oligonucleotide to said DNA fragment; (e) filling in generated overhangs; (f) amplifying said DNA fragments using a third oligonucleotide comprising a first sequence binding to said third sequence of said second oligonucleotide, wherein said third oligonucleotide has a nucleic acid sequence as set forth in SEQ ID NO:2; and (g) sequencing said amplified DNA fragments.

In a further embodiment of the present invention the method of error-free sequencing of DNA comprises the steps of (a) providing a sample comprising DNA; (b) digesting the DNA with a restriction endonuclease under conditions suitable to obtain DNA fragments of similar length, wherein said restriction endonuclease is capable of providing 5' overhangs wherein the terminal nucleotide of the overhang is phosphorylated or 3' overhangs wherein the terminal nucleotide of the overhang is hydroxylated on said DNA fragments and wherein said restriction endonuclease is MseI or an isoschizomer thereof; (c) annealing of the first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second, a third and a fourth sequence, wherein said second sequence of said second oligonucleotide comprises a randomized sequence and wherein said fourth sequence of said second oligonucleotide comprises a restriction site of a site-specific endonuclease; (d) ligating said second oligonucleotide to said DNA fragment; (e) filling in generated overhangs; (e') adding an exonuclease; (f) amplifying said DNA fragments using a third oligonucleotide comprising a first sequence binding to said third sequence of said second oligonucleotide; (f') adding a site-specific endonuclease; and (g) sequencing said amplified DNA fragments.

The invention relates to a method of error-free sequencing of DNA comprises the steps of (a) providing a sample comprising DNA; (a'') digesting the DNA with a proteinase like, e.g., proteinase K; (a''') thermally inactivating the proteinase; (b) digesting the DNA with a restriction endonuclease under conditions suitable to obtain DNA fragments of similar length, wherein said restriction endonuclease is capable of providing 5' overhangs wherein the terminal nucleotide of the overhang is phosphorylated or 3' overhangs wherein the terminal nucleotide of the overhang is hydroxylated on said DNA fragments and wherein said restriction endonuclease may be MseI or an isoschizomer thereof; (c) annealing of the first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second, and a third sequence, wherein said second sequence of said second oligonucleotide comprises a randomized RNA sequence; (d) ligating said second oligonucleotide to said DNA fragment; (e) filling in generated overhangs by addition of reverse transcriptase and a heat stable DNA polymerase; (e') adding RNA digesting enzymes, like, e.g., RNAse H and RNAse If; (e'') adding ligase; (f) amplifying said DNA fragments; and (g) sequencing said amplified DNA fragments.

The invention furthermore relates to the use of the sequenced DNA fragments obtained by the methods of the invention. In particular, the invention relates to the use of the sequence information obtained by the methods of the invention. The sequence information may be used, e.g., in methods for DNA sequence analysis, generation of cell lineage trees or assessment of copy numbers. In particular, the sequence information obtained by the methods of the invention may be used in methods for DNA sequence analysis such as whole genome sequencing, whole exome sequencing, whole regulome sequencing, sequencing-based methylation analysis, sequencing-based breakpoint detection, ChIP sequencing, or targeted sequencing. The method of present invention is particularly useful for all the above-mentioned approaches, where the amount of input nucleic acid, preferably DNA, is strongly limited, i.e. single cell DNA or fractions thereof. Additionally, the method of present invention may be particularly useful for a high throughput sequencing approaches, including deep sequencing approaches, that search for rare sequence variants (i.e. transcipts, transcription variants/isoforms, splicing intermediates, aberrant sites of epigenetic changes, point mutations, indels and other sequence variations and/or mutations) hidden in the background of sequences showing wild type (unchanged) expression profile/epigenetic profile/genotype. Furthermore, the sequence information generated by the methods of the present invention may be used to identify methylation sites within the target DNA.

The present invention also provides for a four-part oligonucleotide, comprising a first, second, third and fourth sequence, wherein the first sequence comprises a fixed sequence, the second sequence comprises a randomized sequence, the third sequence comprises a primer binding site and the fourth sequence comprises a restriction nuclease recognition site and/or restriction site. In accordance with the present invention, the fixed sequence preferably comprises about 4 to 15 nucleotides, the randomized sequence preferably comprises about 3 to 24 nucleotides and the restriction nuclease recognition site and/or restriction site preferably is a recognition site and/or restriction site of a homing endonuclease.

The restriction nuclease recognition site and/or restriction site of the oligonucleotide of the invention, is preferably located on the 5' side of the randomized sequence. It is furthermore preferred that the restriction nuclease recognition site and/or restriction site and the primer binding site, i.e. third and fourth sequence of the oligonucleotide of the invention, are identical and/or overlapping. It is most preferred that the restriction nuclease recognition site and/or restriction site and the primer binding site, i.e. third and fourth sequence of the oligonucleotide of the invention, are 100 percent identical and overlapping.

It is preferred that the four-part oligonucleotide of the invention comprises a fixed sequence comprising a sequence at least 50%, 55%, 60%, 65%, 70%, 75%, 80%, 85%, preferably 90%, 95% or, most preferably, 100% identical to the sequence GTCAGT and/or a randomized sequence and/or a restriction nuclease recognition site comprising a sequence at least 50%, 55%, 60%, 65%, 70%, 75%, 80%, 85%, preferably 90%, 95% or, most preferably, 100% identical to the sequence as shown in SEQ ID NO:3 and/or a primer binding site comprising a sequence at least 50%, 55%, 60%, 65%, 70%, 75%, 80%, 85%, preferably 90%, 95% or, most preferably, 100% identical to the sequence as shown in SEQ ID NO:4. Accordingly, it is preferred that the four-part oligonucleotide of the invention, comprises a sequence at least 50%, 55%, 60%, 65%, 70%, 75%, 80%, 85%, preferably 90%, 95% or, most preferably, 100% identical to the sequence as shown in SEQ ID NOs:5. It is also preferred that the four-part oligonucleotide of the invention comprises a sequence at least 50%, 55%, 60%, 65%, 70%, 75%, 80%, 85%, preferably 90%, 95% or, most preferably, 100% identical to the sequence as shown in SEQ ID NO:12.

It is most preferred that the four-part oligonucleotide of the invention comprises a fixed sequence having the sequence GTCAGT and/or a randomized sequence and/or a restriction nuclease recognition site and/or restriction site having a sequence as shown in SEQ ID NO:3 and/or a primer binding site having a sequence as shown in SEQ ID NO:4. Accordingly, it is preferred that the four-part oligonucleotide the invention, has a sequence as shown in SEQ ID NO:5. It is also preferred that the four-part oligonucleotide has a sequence as shown in SEQ ID NO:12.

It is most preferred that the four-part oligonucleotide of the invention comprises a fixed sequence and/or a randomized sequence and/or a restriction endonuclease recognition site and/or a primer binding site, wherein the primer binding site has a sequence at least 50%, 55%, 60%, 65%, 70%, 75%, 80%, 85%, preferably 90%, 95% or, most preferably, 100% identical to the sequence as shown in SEQ ID NO:13. Accordingly, it is most preferred that the four-part oligonucleotide of the invention comprises a sequence at least 50%, 55%, 60%, 65%, 70%, 75%, 80%, 85%, preferably 90%, 95% or, most preferably, 100% identical to the sequence as shown in SEQ ID NO:14.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual*, Cold Spring Harbor Laboratory Press, Cold Spring Harbor, N.Y. (1990).

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the figures individually, although they may not have been described in the afore or following description. Also, single alternatives of the embodiments described in the figures and the description and single alternatives of features thereof can be disclaimed from the subject matter of the other aspect of the invention.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The present invention is also illustrated by the following figures.

FIG. 1. Oligonucleotide Sequences.

The figure shows oligonucleotide sequences of the first, second and third oligonucleotide as may be used in the methods of the present invention. In addition, the sequence of the four-part oligonucleotide is shown. The oligonucleotide $DSL_{12}$ has the sequence as shown in SEQ ID NO: 1. The oligonucleotide $DSL_9$ has the sequence as shown in SEQ ID NO: 6. The DSPCR oligonucleotide has the sequence as shown in SEQ ID NO: 2.

FIG. 2. Assay accuracy of three PCR markers selected to predict a successful metaphase CGH experiment FIG. 3. Detection of specific sequences after WGA FIG. 4. Quality control assay and prediction of WGA quality in clinical samples.

FIG. 5. Selection of the optimal oligonucleotide design for efficient sample preparation (A,B) Results of the 3-plex PCR performed on samples processed with either $DSL_{12}$-$DSS_6$ (A) or $DSL_9$-$DSS_5$ (B) oligonucleotide duplex. Samples 1-10 indicate DNA samples originating from a single-cell of a healthy donor. Samples P1 and P2 were generated using pools of cells. + and − indicated positive and negative control, respectively. (C-D) aCGH profiles of single-cell of a healthy donor (C) and single-cell of OE-19 cell lines (D). All autosomes are shown. Both samples were generated with $DSL_{12}$-$DSS_6$.

Figure 6:
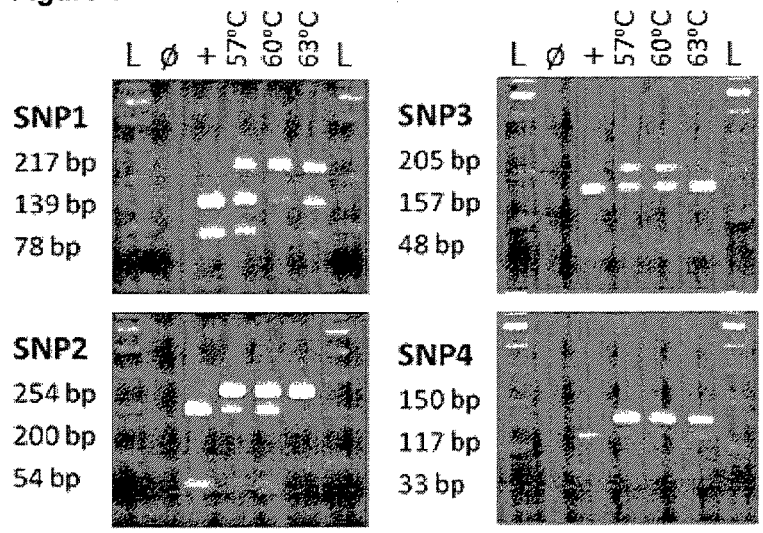

FIG. 6. Analysis of the allelic drop-out (ADO) rate. Results of RFLP-PCR specific for four SNP markers (SNP1-SNP4). Three randomly selected samples, each originating from single-cells were included in the analysis. Each sample was subjected to a different variant of the primary PCR varying in the temperature of the annealing step. L indicates the position of the DNA size marker, Ø indicates a negative PCR control and + positive control of the restriction digest.

Figure 7:
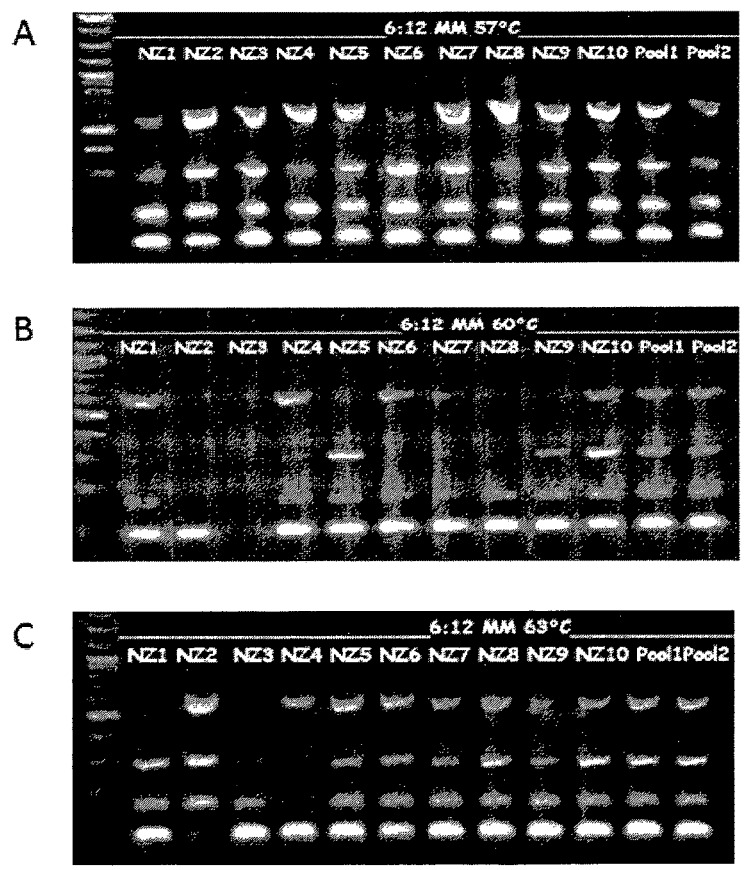

FIG. 7. Impact of the oligonucleotide annealing temperature on the annealing of the DSL12 oligonucleotide during the primary PCR.

A,B,C) Results of the 4-plex quality control PCR of samples processed with three variants of the primary PCR, differing in the terms of temperature of the oligonucleotide annealing: 57° C. (A), 60° C. (B), 63° C. (C). Each of the samples NZ1-NZ10 originate from individually processed single-cells of a healthy male donor, whereas the samples Pool1 and Pool2 were generated with a pool of cells.

Figure 8:
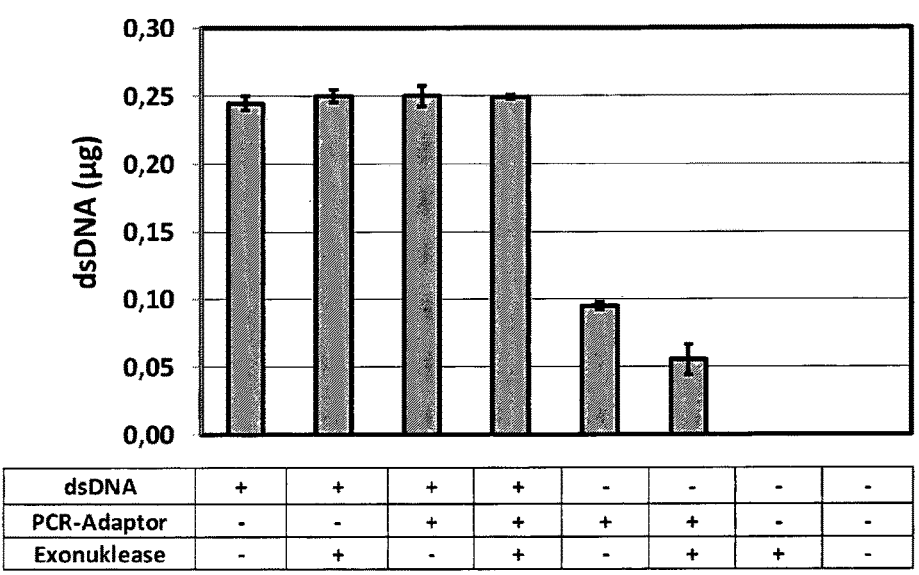

FIG. 8. Performance of the Exonuclease in the PCR reaction buffer used for the primary PCR.

Double stranded PCR product (dsDNA) with or without addition of PCR adaptors was treated with Exonuclease I. Note no effect of the Exonuclease I treatment on the yield of dsDNA and reduction of the PCR-adaptor content in the reaction.

FIG. 9. Detection of DSL oligonucleotide sequence after amplification of single cell amplicons (A,B,C) Sequences of randomly selected sequences representing three specific MseI restriction fragments flanked by $DSL_{12}$ sequences. Color code indicates the position of the oligonucleotide sequences: yellow—binding sequence of the DSPCR primer including the I-SceI site; green—randomized barcode sequence, violet—fixed 3'-end. Note that the sequence of the randomized barcode is each time different proving that unique barcodes were indeed introduced. The sequence of part A corresponds to SEQ ID NO: 7, the sequence of part B corresponds to SEQ ID NO: 8 and the sequence of part C corresponds to SEQ ID NO: 9.

FIG. 10. Conditions for Proteinase K digestion.

FIG. 11. Conditions for MseI digestion

FIG. 12. Conditions for Annealing of the PCR adaptors

FIG. 13. Conditions for ligation

FIG. 14. Conditions for primary PCR (variant without Exonuclease treatment)

FIG. 15. Conditions for primary PCR (variant including Exonuclease I treatment)

Figure 16:
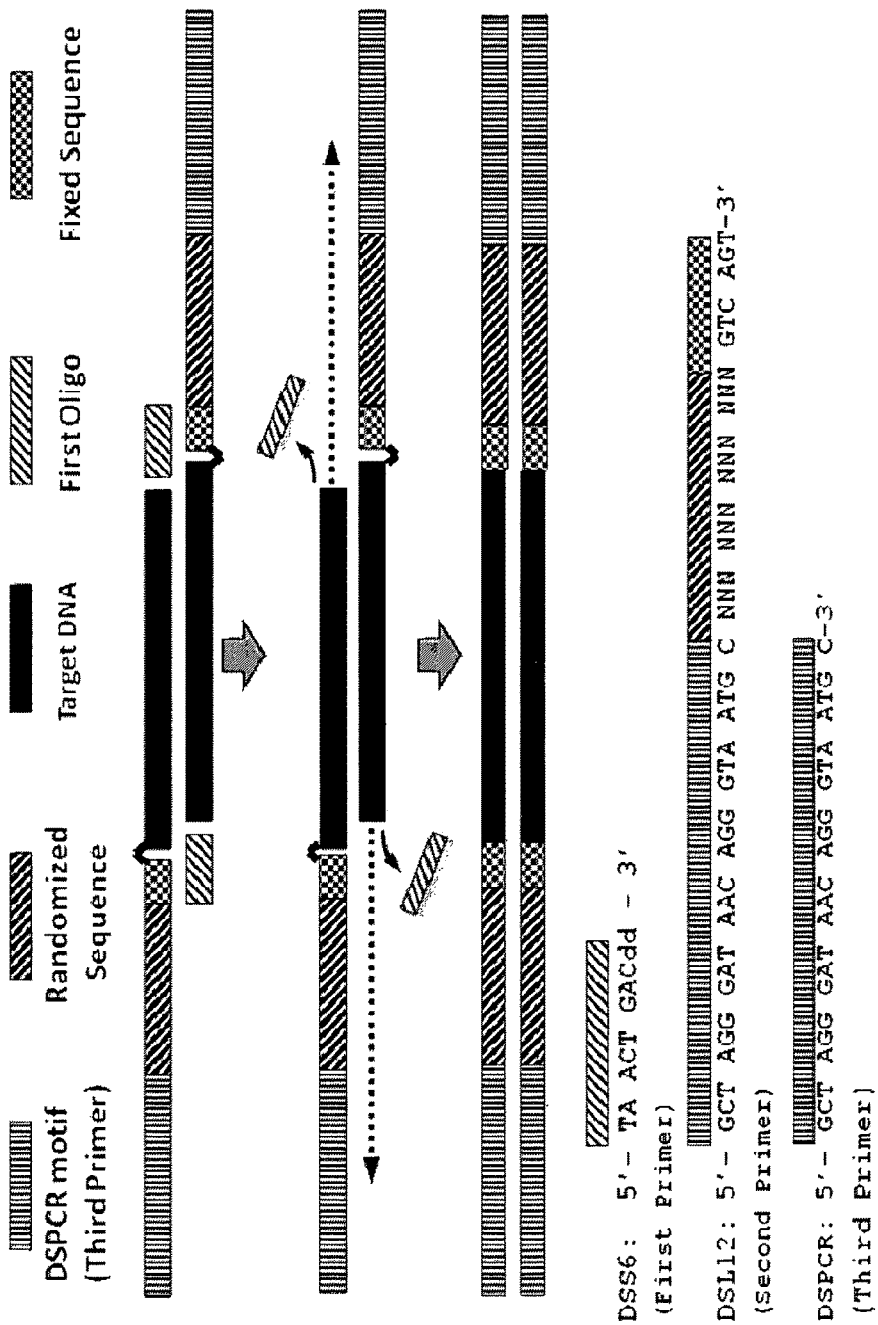

FIG. 16. Illustration of binding and ligation of oligonucleotides of the invention to target DNA Overview of the mechanism underlying the ligation of the PCR-adaptors and the subsequent fill-in reaction. Due to lack of phosphate at the 5'-end of the first oligonucleotide—DSS—it cannot be covalently ligated to the 3'-end of the target DNA sequence. Ligation events occur preferentially between 3'-end of the second oligonucleotide (DSL, SEQ ID NO: 1) and the 5'-end of the target DNA sequence. Additionally, modification of the 3'-end of the first oligonucleotide (introduction of the 2',3' dideoxynucleotide), prevents any priming event initiated by this oligonucleotide. During the fill-in step (68° C.), the DSS oligonucleotide disassociates from its binding partners, allowing DNA polymerase to synthesize the sequence complimentary to the DSL oligonucleotide. The subsequent PCR-based amplification is conducted with the use of the third oligonucleotide (DSPCR, SEQ ID NO: 2), which is complementary to the third sequence of the DSL oligonucleotide.

Figure 17:
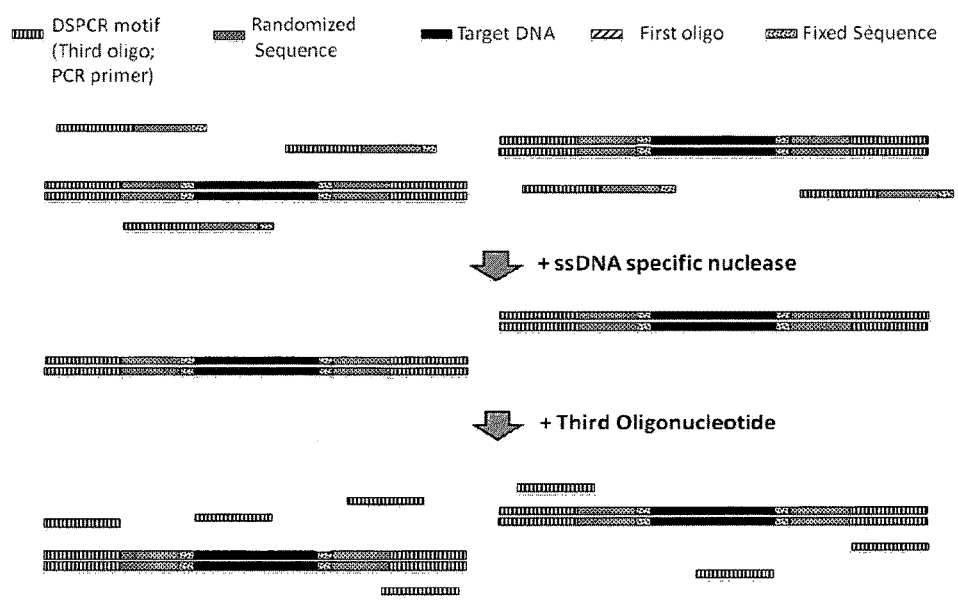

FIG. 17. Illustration of use of exonuclease in order to degrade second oligonucleotide Utilization of a single strand exonuclease following the fill-in reaction of the PCR-adaptor sequence facilitates removal of the residual second oligonucleotide (unbound to the target sequence. The removal of the unligated second oligonucleotide prevents its interference with the subsequent amplification by the non-degenerated third oligonucleotide as primer.

Figure 18:
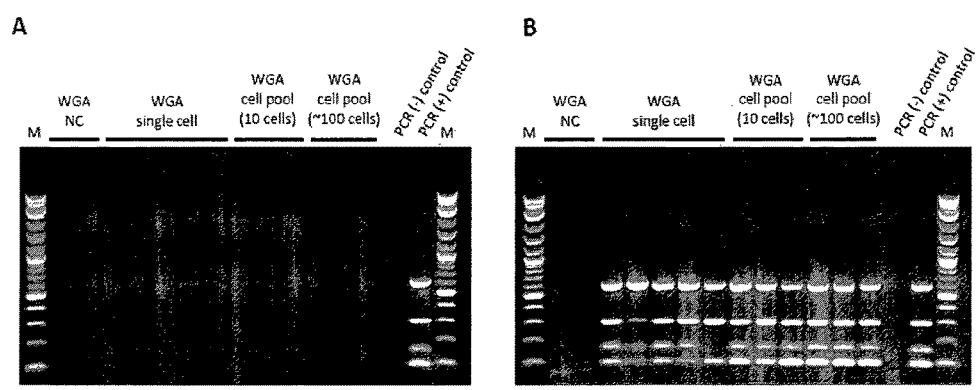

FIG. 18. Application of the method to whole genome amplification (WGA) and comparison with a method of the state of the art Photographs presents results of control PCR performed on WGA products generated with either the method described in Jones (1997) BioTechniques 22:938-946 and U.S. Ser. No. 08/742,755 (A) or the method of the present invention (B). In both cases WGA products were generated with variable amount of template DNA (i.e. single-cell, pool of 10 cells and pool of ~100 cells). Lanes M: molecular weight marker (2-log DNA ladder; New England Biolabs); lane 1-2: negative (no template) controls of WGA; lane 3-7: WGA products—each generated with DNA of a different single cell; lanes 8-10: WGA products generated with pools of 10 single cells; lane 11-13—WGA products generated with pools of ~100 cells); lane (−)—PCR negative control; lane (+)—PCR positive control. Experiments were performed as described in Example 10.

FIG. 19a-d. Illustration of error correction via grouping of sequencing reads sharing the same randomized sequence Sequencing reads were aligned against the human genome assembly 19 and grouped based on the randomized sequence identified within their respective adaptor sequence. Shown are small sections of reads mapping to (a) chromosome 6 from position 124,934,321 to 124,934,396, (b) chromosome 22 from position 39,277,551 to 37,277,608, (c) chromosome 22 from position 18,455,108 to 18,455,137 and position 18,455,218 to 18,455,247 and (d) chromosome 22 from position 42,820,701 to 42,820,754. In each example, the respective reference sequence at the respective position is shown on top of the reads. Asterisks "*" below sequences of read groups indicate positions within a group of randomized sequences where 100% of the bases are in agreement with the reference, while gaps " " indicate positions within a group of randomized sequences which differ in a minority from the reference. These errors are considered as sequencing- or amplification-errors and would therefore need error-correction. An "X" below the sequences of read groups further indicates positions within all reads in the alignment where the majority of reads in at least one group of randomized sequences differ from the reference. These are either considered as SNPs (if the difference occurs in only one group of randomized sequences) or mutations (if the difference consistently occurs in all groups of randomized sequences). The sequences in part A of the figure correspond to (from top to bottom), SEQ ID NOs: 138, 139, 15, 16, 17, 18, 19, 20, 21, 22, 23, 24, 25 and 26, respectively. The sequences in part B of the figure correspond to (from top to bottom) SEQ ID NOs: 27, 28, 29, 30, 31, 32, 33, 34, 35, 36, 37, 38, 39, 40, 41, 42, 43 and 44, respectively. The sequences in part C of the figure correspond to (from top to bottom) SEQ ID NOs: 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 and 95, respectively. The sequences in part D of the figure correspond to (from top to bottom) SEQ ID NOs: 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136 and 137, respectively.

The present invention is additionally described by way of the following illustrative non-limiting examples that provide a better understanding of the present invention and of its many advantages. The following examples are included to demonstrate preferred embodiments of the invention. It should be appreciated by those of skill in the art that the techniques disclosed in the examples which follow represent techniques used in the present invention to function well in the practice of the invention, and thus can be considered to constitute preferred modes for its practice. However, those of skill in the art should appreciate, in light of the present disclosure, that many changes can be made in the specific embodiments which are disclosed and still obtain a like or similar result without departing from the spirit and scope of the invention.

Figure 20:
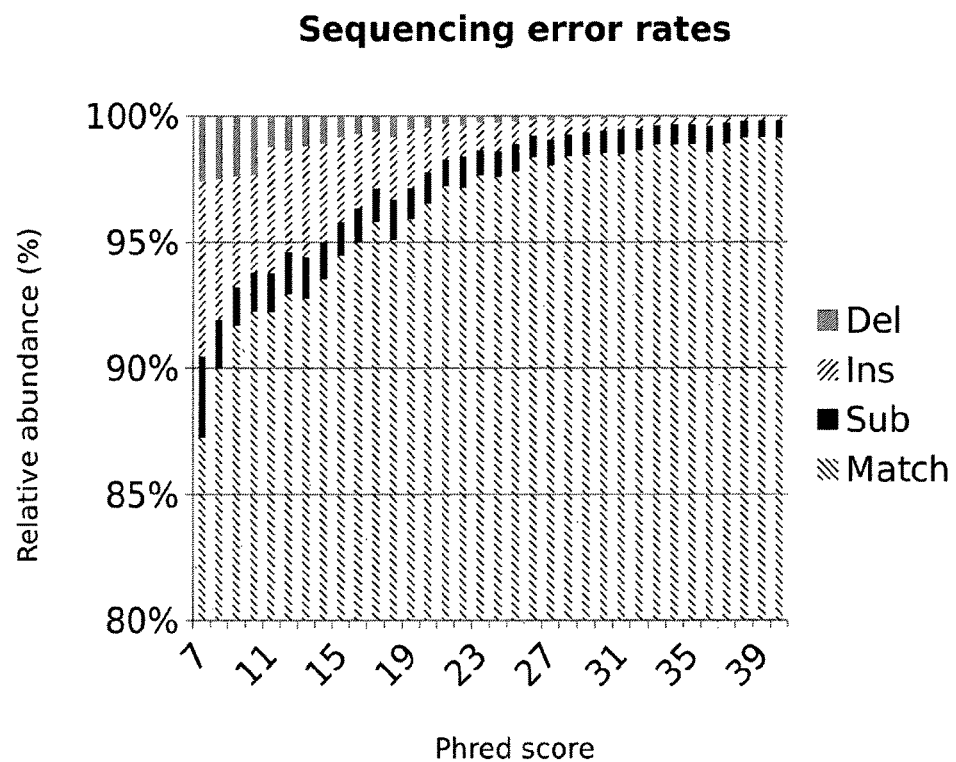

FIG. 20. Sequencing error rates

Read sequences from an error-free sequencing run were mapped to the human genome assembly 19. Shown is the relative abundance of deletions (Del), insertions (Ins), mismatches/substitutions (Sub) and matches (Match) of mapping positions in relation to the phred score of the read base mapping to this position. This indicates a correlation between the increasing numbers of variations from the reference (Del/Ins/Sub) to the sequencing quality and further supports the need for error correction.

Unless otherwise indicated, established methods of recombinant gene technology were used as described, for example, in Sambrook, Russell "Molecular Cloning, A Laboratory Manual", Cold Spring Harbor Laboratory, N.Y. (2001) which is incorporated herein by reference in its entirety.

EXAMPLE 1—DESIGN OF A METHOD OF ERROR-FREE SEQUENCING OF DNA

The crucial component of the method is the design of oligonucleotides that enable the amplification of single DNA molecules and the identification and removal of artifactual mutations. These oligonucleotides are bound to single DNA molecules via ligation. The removal of artifactual mutations is based upon the identification of complementary DNA strands that formed a double-stranded DNA molecule before manipulation of the sample (e.g. for example in a single cell). Therefore, the oligonucleotides that are added to the DNA molecule of interest form a double stranded molecule at the site of ligation. For simplicity oligonucleotides forming these adaptors for error-free sequencing were termed DSL or DSS, for duplex sequencing oligonucleotide long and duplex sequencing oligonucleotide short, respectively. The sequences of both oligonucleotides are outlined in FIG. 1. Both oligonucleotides are partially complementary to each other allowing formation of oligonucleotide-oligonucleotide duplexes, which are used as adaptor in a ligation-mediated PCR approach (FIG. 1). In the duplex structure, the DSS oligonucleotide forms 5'-overhang, which is compatible with the restriction sites introduced into the genomic representation by restriction endonuclease (for the restriction enzyme Mse I, these bases are TA), allowing more efficient ligation of the PCR-adaptors. The remaining bases are complementary to the DSL oligonucleotide. We use a subscript m (DSSm) to indicate the length of the complementary sequence. The DSS oligonucleotide may contain a dideoxynucleotide to prevent its elongation during the polymerization steps (FIG. 1). The DSL oligonucleotide is composed of three to four parts. The sequence on the 3'-end is a fixed sequence that is responsible for formation of oligonucleotide-oligonucleotide duplexes with the DSS oligonucleotide. It can be varied and also used to generate oligonucleotides of varying identity for example to tag cells of a specific individual (note that in this case the DSS oligonucleotide needs to have the complementary sequence). The middle section of the DSL oligo contains a randomized sequence, which is used as barcode to uniquely mark each oligonucleotide in the reaction that is ligated to the target DNA. The length of the barcode may vary. For the examples here we add the subscript n ($DSL_n$) to indicate the number of random bases. The third, most 5'-located sequence of the oligonucleotide may contain a site-specific motive for a restriction enzyme, for example of a homing endonuclease, such as I-SceI. This 5'-end of the $DSL_n$ oligonucleotide is designed to allow efficient PCR-based amplification of the entire sample representation.

To enable the amplification, the following steps are used:
1) formation of the adaptor of DSL and DSS
2) Ligation of the adaptor; in the example here the DSL is being covalently ligated while the DSS is not. Thereafter, the shorter DSS oligonucleotide will be released from the base-pairing at a mild denaturing step during polymerization (step 3).
3) Polymerization of the complementary sequence (fill-in reaction) of the DSL oligonucleotide. During this step the barcode is being generated as double stranded barcode.
4) A third oligonucleotide is used for amplification that binds the PCR-primer binding region at the 5'-region of the DSL oligonucleotide.

EXAMPLE 2 GENERAL OUTLINE OF A METHOD OF ERROR-FREE SEQUENCING OF DNA

The procedure used for preparation of genetic representation(s) allowing subsequent error-free sequencing consisted of the following steps:
(a) Access to DNA by removal of the cellular structures and proteins that encapsulate the DNA material (typically performed using proteolytic enzymes i.e. proteinase K and/or detergents)
(b) Digestion of the DNA material using a (frequent cutting restriction enzyme; here MseI)
(c) Annealing of $DSL_n$ and $DSL_m$ oligonucleotides
(d) Ligation of the $DSL_n$-$DSL_m$ oligonucleotide duplexes to the DNA material under inspection
(e) Optional: Digestion of unbound (DSL/DSS) oligonucleotides using exonuclease or other single strand DNA (ssDNA) specific enzymes or RNAse H in case of DNA/RNA oligos.
(f) Amplification of the targeted genomic representation(s) using a universal primer (here termed DSPCR), whose sequence is identical to the 5'-primer binding region of the $DSL_n$ oligonucleotide.

The complete protocol or selected parts of it can be used for various types of samples e.g. single-cells, a multitude of single cells, cell-free DNA, exosomal DNA, chemically fixed tissue specimens (i.e. formalin fixed paraffin embedded tissue samples), etc.

EXAMPLE 3—SAMPLES PROCESSED WITHOUT THE ADDITION OF EXONUCLEASE

Single cells have been isolated from peripheral blood of a healthy individual or harvested from adherent cell culture of OE-19 esophageal cancer cells. A single cell was picked in 1.0 µL of PBS and transferred into a reaction tube containing 2.0 µL of proteinase K digestion buffer (10 mM Tris acetate, pH 7.5, 10 mM Mg acetate, 50 mM K acetate (0.2 µL of 10×One-Phor-All-Buffer-Plus buffer); 0.67% Tween 20; 0.67% Igepal; 0.67 mg/ml Proteinase K). All subsequent steps of the protocol were performed in a PCR machine with a heated lit. Proteinase K digestion was performed for 10 h at 42° C., followed by an inactivation step at 80° C. for 10 min. Next, single cell DNA was subjected to digestion with MseI (Fermentas) restriction endonuclease by adding 0.2 µL of 10×One-Phor-All-Buffer-Plus buffer, 10 U of MseI (New England Biolabs) and $H_2O$ to a total volume of 5.0 µL. The restriction digestion was performed for 3 hours at 37° C. and heat-inactivated at 65° C. for 5 min. Preparation of the adaptors for ligation mediated PCR was achieved by annealing of $DSL_n$ and $DSS_m$ oligonucleotides. For this purpose 0.5 µL of 100 µM stock solution of each of the oligonucleotide was mixed with 1.0 µL of $H_2O$. The annealing was initiated at 65° C. and continued at continuously decreasing temperature, with a ramp of 1° C./min, down to 15° C. Annealed oligonucleotides were supplemented with 0.5 µL of DSPCR oligonucleotide [100 µM stock solution], 1 µL of ATP (10 mM) and 1 µL of T4-DNA ligase (5 U; Roche). Subsequently premixed oligonucleotide/ATP/ligase mixture was added to fragmented DNA representation and ligated over night at 15° C. The subsequent PCR reaction was started after adding 3 µL of PCR buffer (Expand Long Range Buffer 1, Roche), 2 µL of dNTPs (10 mM), 5 U of Pwo/Taq DNA polymerase mix (PolMix, Expand Long Range Buffer 1, Roche) and $H_2O$ to a total volume of 50 µL and run for 47 cycles in a PCR machine. Details of the cycling procedure used in the primary PCR are outlined in FIG. 14.

EXAMPLE 4—SAMPLE PREPARATION INCLUDING EXONUCLEASE TREATMENT

The inclusion of a barcode with 3 to 18 random bases marks basically every ligated DNA molecule of a single or few cells in a way that each resulting sequence is unique. Therefore, the DSL oligonucleotide cannot be used as a PCR oligonucleotide, because either the unique barcode is lost or amplification efficiency is poor. Moreover, the DSL oligonucleotide with intact barcode may negatively affect the PCR reaction by unwanted random priming events.

To prevent unwanted binding of the DSL oligonucleotide one can add an exonuclease step after the fill-in reaction and before the exponential amplification of the sample. In this embodiment of the procedure the steps of proteinase K digestion and MseI digestion remained unchanged. Annealing of the oligonucleotide sequences was composed of 0.5 µL of 10×One-Phor-All-Buffer-Plus buffer, 0.5 µL of $DSL_n$ and $DSS_m$ oligonucleotide (100 µM each), and 1.5 µL $H_2O$. Identically, to the previous variation of the procedure, the annealing was initiated at 65° C. and continued at continuously decreasing temperature, with a ramp of 1° C./min, down to 15° C. Subsequently, annealed oligonucleotides were mixed with the product of the MseI digestion and ligated over night at 15° C. The subsequent primary PCR reaction was assembled by adding 3.0 µL of PCR buffer (Expand Long Range Buffer 1, Roche), 2 µL of dNTPs (10 mM), 5 U of Pwo/Taq DNA polymerase blend (PolMix, Expand Long Range Buffer 1, Roche) and 34.0 µL of $H_2O$. Following a fill-in step (3 min at 68° C.), 0.5 µL Exonuclease I (20 U/µL) was added to remove the unbound oligonucleotides. Exonuclease digestion was performed at 37° C. for 30 minutes and heat-inactivated at 85° C. for 15 minutes. Next, 0.5 µL of DSPCR oligonucleotide (100 µM) was added and the PCR was initiated. The specification for the cycling procedure used are outlined in FIG. 15.

EXAMPLE 5—QUALITY CONTROL OF SAMPLES FOR ERROR-FREE SEQUENCING

A surrogate assay that predicts the quality of the whole genome amplification (WGA) was previously developed. To establish this assay, a metaphase CGH, array CGH and allelic drop-out rates to assess for each individual cell the quality of the WGA were used. In brief, in order to devise an adequate test to assess a reliable and homogeneous whole genome amplification of single cell DNA with Ampli1™ the following experiment was performed: From the existing single cell WGA biobank, 72 WGA products of single disseminated cancer cells (DCC) isolated from bone marrow of breast cancer and prostate cancer patients were selected, as well as from lymph nodes of melanoma patients. From each of the three tumor types, 12 DCC that had been successfully hybridized on human chromosomes in previous CGH experiments (n=36), and 3×12 DCC that failed in CGH experiments were selected. Eight different oligonucleotide pairs for MseI restriction fragments located on different chromosomal regions and with different fragment length were designed, ranging from 239 bp to 1936 bps. Specific PCR with eight oligonucleotide pairs on all the selected DCC were performed and the results with known CGH result correlated. Three oligonucleotide pairs were found to be able to predict a successful metaphase CGH experiment with a specificity of 94% and a sensitivity of 97%, if a single cell WGA product was positive for at least 2/3 markers (FIG. 2).

The assay was validated in a cohort of 100 diploid non-cancer cells that have been isolated and their DNA amplified between 1999 and 2008. Twenty-two WGA products of single cells predicted by the selected three oligonucleotide pairs to enable CGH analysis and 10 WGA products of single cells predicted to fail were selected. The performance of CGH was correctly predicted in all 32 cases. Later, a fourth pair of PCR oligonucleotides located on a 192 bp long MseI restriction fragment encompassing the frequently mutated Codon12/13 of the KRAS gene and designed a 4 marker multiplex PCR assay (Ampli1™ QC kit) to predict genome integrity of isolated cells was included.

Then, 88 single mononuclear cells from peripheral blood of a male donor were isolated using manually controlled micromanipulator, genomic DNA was amplified and the quality of amplification assessed with Ampli1™ QC kit on freshly isolated and unfixed cells. Results showed that 83/88 (94.3%) of the cells displayed two or three of the QC band (FIG. 3).

The final QC assay assigns a genomic integrity index (GII) of 0, if no band is amplified; of 1, if one band is amplified; of 2 if two bands are amplified; of 3, if three bands are amplified; of 4, if four bands are amplified. (FIG. 3). The GII were tested on circulating tumor cells from patients isolated by the CellSearch system. All cells were investigated with several downstream analyses, i.e. qPCR, targeted Sanger sequencing and aCGH. Again the assay was perfectly suited to assess the quality of the samples.

The multiplexed PCR-based QC-assay was used to determine the quality of samples for the error-free sequencing. This reaction assesses the presence of three different loci in the human genome. The positive rate of the multiplex reaction correlates with success rate of the multiple downstream application, thereby it can be used as surrogate marker for the successful whole genome amplification.

To further assess the quality and performance of sample preparation, the rate of allelic dropout (ADO) resulting from bias introduced during the sample preparation was analysed. For this purpose, four different SNP markers were chosen, tested as heterozygous in all specimens included in the test series and tested for their presence in the sample in a RFLP-PCR assay.

EXAMPLE 6—OPTIMIZATION OF THE SAMPLE PREPARATION PROCEDURE FOR ERROR-FREE SEQUENCING

Determination of the Optimal Oligonucleotide Design.

The unwanted priming of the DSL oligonucleotide depends on the ratio of the length of 3'-fixed sequence of the DSL oligonucleotide and the length of the barcode. The shorter the 3'-fixed sequence the weaker is the 3'-binding of bases crucial for Taq-polymerase extension. The longer of the barcode the less likely is the chance that fully complementary DSL oligonucleotides bind to DNA-adaptor products during PCR. Therefore, short barcodes may work better with short fixed sequences and longer fixed sequences may require longer barcodes.

To test how the length of the $DSS_m$ oligonucleotide influences the performance of the primary PCR, two variants of the oligonucleotide, $DSS_5$ and $DSS_6$, with the length of 5 or 6 bases in addition to the two bases reconstituting the TTAA motif, respectively, were tested.

Two oligonucleotide combinations $DSL_{12}$-$DSS_6$ and $DSL_9$-$DSS_5$ were tested on ten single-cells and two cell pools of a healthy male donor. The performance of both oligonucleotide duplexes was assessed using the multiplex PCR (FIG. 5).

The results of the QC assay indicate that the adaptor composed of $DSL_{12}$ and $DSS_6$ provide reproducibly high-quality PCR products, whereas utilization the $DSL_9$-$DSS_5$ seems to be less suited (FIG. 5A-B). The comprehensive amplification of a single cell genome using $DSL_{12}/DSS_6$ was confirmed in aCGH experiments (FIG. 5C-D). For this reason further experiments were performed with $DSL_{12}$-$DSS_6$ oligonucleotide combination only.

Determination of the Optimal Temperature for Oligonucleotide Annealing During the Primary PCR.

To further optimize the performance of the adaptor-mediated PCR, the cycling conditions for the primary PCR were tested. The incorporation of the randomized tag of the $DSL_n$ oligonucleotide resulted in variable annealing kinetics of the different oligonucleotide variants. Therefore, proper selection of the annealing condition may be crucial for the success of the PCR. To find the most optimal setting, three different annealing temperature were tested: 57° C., 60° C. and 63° C. Single cell samples were processed with the modified primary PCR. Subsequent SNP analysis showed comparable allelic drop-out rates independent of the annealing temperature used (FIG. 6). This suggests that the protocol enables to completely amplify a single cell genome with rare allelic losses. Therefore, coverage of the genome appears to be excellent.

However, the quality assessment of PCR products using the multiplex PCR revealed that increased annealing temperatures may have a slightly negative impact on the primary PCR (FIG. 7). The samples showed the best quality, when annealing temperature of 57° C. was used during the primary PCR (FIG. 7). Consequently, this setting was used for further experiments.

EXAMPLE 7—ADDITIONAL EXONUCLEASE TREATMENT

As already mentioned, presence of the unbound $DSL_n$ oligonucleotide in the primary PCR may impede some downstream applications or occasionally the efficiency of the amplification reaction. To prevent that, the effects of Exonuclease I digestion step introduced between the fill-in reaction and the initiation of the exponential amplification of the restriction fragments in the primary PCR was tested. By using this approach it was attempted to eliminate the unbound oligonucleotide prior to proceeding with the PCR-based amplification of the genomic representation of the samples. Initial tests with the Exonuclease I indicated that the enzyme does not affect the double-stranded DNA fraction in the PCR reaction and allows removal of the unbound PCR adaptors (FIG. 8).

EXAMPLE 8—DIRECT PROOF FOR INTRODUCTION OF THE BARCODE INTO SINGLE CELL DERIVED AMPLICONS

To demonstrate that the Mse I restriction fragments were indeed marked with the barcode, three randomly selected restriction fragments from a single cell sample generated using the $DSL_{12}$ oligonucleotide were sequenced. To isolate individual fragments, the size selected (fragments larger than 300 bp only) representation of the single-cell genome was cloned into a pGEM T-Easy vector. After transforming the *E. coli* bacteria with these construct and colorimetric X-Gal based selection of the transformed colonies, three colonies were randomly selected for further testing. Upon isolation of plasmid DNA, subsequent sequencing revealed sequences harbouring human genomic sequences flanked by the $DSL_{12}$ oligonucleotide and its complementary sequences (FIG. 8). As expected the randomized barcode sequence differed for all three fragments proving that our new approach allows unique tagging of the individual restriction fragments in the genomic representation originating from single-cell DNA (FIG. 9). Likewise the fixed patient-tag sequence and the I-SceI site could be retrieved.

EXAMPLE 9—USE OF DNA/RNA OLIGONUCLEOTIDES

The use of a DNA/RNA oligonucleotide is also envisaged. Such a method comprises the following steps:
1) Protease digest of cell-free DNA;
2) Restriction, using e.g. MseI;
3) Adaptor ligation, wherein the second oligonucleotide is a DNA/RNA oligonucleotide that comprises a first sequence consisting of DNA, a second sequence consisting of RNA and a third sequence consisting of DNA. Accordingly, the random sequence of the second oligonucleotide consists of RNA;
4) Addition of reverse transcriptase+(heat stable) DNA Polymerase and deoxynucleotides to generate double strands, whereby a DNA:DNA-RNA:DNA-DNA:DNA molecule at the ligated second oligonucleotide is created. Accordingly the complementary DNA strand to the randomized sequence RNA strand is created;
5) Addition of RNAse H to digest DNA/RNA double stranded hybrids;
6) Addition of RNAse If to digest single stranded RNA of the free adaptors made of first and second oligonucleotide;
7) After removal of RNA sequence of the ligated second oligonucleotide, the remaining DNA parts of the second oligonucleotide are linked again by the DNA polymerase;
8) Addition of ligase to link extended part of the second oligonucleotide with fixed region of second oligonucleotide;
8) Addition of remaining PCR reagents;
9) Addition of the third oligonucleotide. If the RNAse steps are efficient, the PCR primer is created during the reaction. Accordingly, there if the RNAse steps are efficient, there is no need to add a third oligonucleotide.

EXAMPLE 10—APPLICATION TO WHOLE GENOME AMPLIFICATION (WGA)

Performance of WGA generated by the method of the present invention was assessed using a multiplex PCR assay specifically designed to test the quality of single-cell WGA products; see Polzer et al. (2014) EMBO Mol Med. October 30; 6(11):1371-86. This test assesses the presence of four genetic loci (KRAS, D5S 2117, KRT19 and TP53) in the WGA products. Presence of all four sequences (4 positive bands) is indicative for high-quality product. Conversely, lack of any product in the control PCR indicates poor quality of the WGA products. As comparison, a protocol was performed as described by Jones (1997) BioTechniques 22:938-946 and in U.S. Ser. No. 08/742,755. In the following, the protocol described in the prior art, namely Jones (1997) BioTechniques 22:938-946 and U.S. Ser. No. 08/742,755, is indicated as (A) while the experiment which was conducted using the method of the present invention is referenced as (B).
Providing DNA Sample The method described in Jones (1997) BioTechniques 22:938-946 and U.S. Ser. No. 08/742,755 was compared to the method of the present invention. Both methods were used to amplify 13 samples with varying amount of starting material: five reactions with single peripheral blood lymphocytes (PBLs) from a normal donor, three pools of 10 PBLs and three pools of 100 PBLs were lysed simultaneously in duplicates in individual vessels to release the double-stranded genomic deoxyribonucleic acid (DNA).
DNA Restriction
(A) In accordance with the method described in Jones (1997) BioTechniques 22:938-946 and U.S. Ser. No. 08/742,755, the isolated DNA was digested with a restriction enzyme whose cleavage site is separate from its recognition site (here Bse RI), thereby creating double strand molecules having a single strand overhang sequence corresponding to the restriction site of the used enzyme. Subsequent to the restriction, the enzyme was inactivated according to the information provided by the manufacturer. In the experimental setting, the Bse RI concentration was ~0.151 U/pg, ~0.015 U/pg and ~0.001 U/pg of DNA for single cell DNA, DNA originating from cell pool of 10 PBLs and 100 PBLs, respectively (1 unit is defined as the amount of enzyme required to digest 1 µg of λ DNA in 1 hour at 37° C. in a total reaction volume of 50 µl). Restriction digestion was conducted for 3 hours at 37° C. in a reaction volume of 5 µL.
(B) In parallel, the isolated DNA was treated as described herein, i.e. using the MseI restriction enzyme at the concentration of ~1.5 U/pg, ~0.15 U/pg and ~0.015 U/pg of DNA for single cell DNA, DNA originating from cell pool of 10 PBLs and 100 PBLs, respectively (1 unit is defined as the amount of enzyme required to digest 1 µg of A DNA in 1 hour at 37° C. in a total reaction volume of 50 µl). Restriction digestion was conducted for 3 hours at 37° C. in a reaction volume of 5 µL.
PCR Adapter
(A) An adaptor corresponding to adaptor set 1 (as shown in Table 2 of Jones (1997) BioTechniques 22 (5), 938-946 and listed in Example 2 of U.S. Ser. No. 08/742,755) was generated as described in the Materials and Methods section of the Jones et al. publication with the exception that instead of using four different adaptors, each carrying a fixed nucleotide at the 3'-terminal position of the upper strand, only one adaptor with upper strand presenting two virtual bases (N) at the 3'-terminal position was used.

Annealing of Adapter
(A) Double stranded adapters were generated by annealing of the upper and lower strand oligonucleotides according to the procedure described in Jones D H et al., BioTechniques 22 (5), 938-946.
(B) In parallel, the first and second oligonucleotide of the invention were annealed using the following protocol: step 1—30 s at 80° C. followed by step 2—incubation step at 65° C. for 1 min and step 3: cooling to 15° C. with a constant ramp temperature ramp of 1° C./min.

Ligating of Adapter

For both experiments, adaptors were ligated to the products of restriction enzyme digestion in the presence of 1 µL of ATP (10 mM) and 5 U of T4 DNA ligase.

PCR Amplification
(A) The ligated double-strand molecules were amplified by a primer specific for adaptor set 1, whereby the sequence was homologous to the sequence of the upper strand of the adaptor served as the identification tag.
(B) The ligated double-strand molecules were amplified by a primer specific for oligonucleotide 2, whereby the terminal part of oligonucleotide 2 served as the primer binding tag. That is, the ligated double-strand molecule was amplified using a third oligonucleotide as used in the methods of the present invention.

Evaluation

The suitability of both methods for WGA was assessed by the QC2 multiplex PCR assay (Polzer et al 2014; EMBO Molecular Medicine (2014) 6, 1371-1386).

Results

Negative results of the multiplex PCR assay in all samples amplified by the method described in Jones D H, BioTechniques 22:938-946 and U.S. Ser. No. 08/742,755 indicate that this approach is not suitable for whole genome amplification and consequently is unable to result in error-free sequencing of an entire genome. Therefore, the application of the therein described method is limited only to sequencing of selected and pre-amplified (e.g. by PCR) genomic loci and not for analysis of entire genomes.

In contrast, positive results of the multiplex assay obtained when applied to WGA products generated using the method of the present invention show that this technology is suitable for whole genome amplification of entire genomic sequence representation. Moreover, the method of the present invention may subsequently be used for error-free sequencing of the entire genome. As is shown in FIG. 18, the method of the present invention enables the skilled person to amplify DNA and subsequently retrieve the sequence information from samples, where only low amounts of starting material are present. In particular, the methods of the present invention are able to amplify the DNA of single cells whose sequence information may then be retrieved using the methods as provided herein.

EXAMPLE 11—ERROR-FREE SEQUENCING OF THE DNA OF SINGLE CELLS

In order to demonstrate the feasibility of error correction using a randomized sequence as barcode/identifier as part of the second oligonucleotide used in the methods of the present invention, two experiments were performed. For these, randomized sequence containing adaptors were ligated to ~6 pg MseI digested DNA either from a single cell or from FACS sorted human chromosome 22. MseI fragments were afterwards amplified using Ampli1™ and subsequently sequenced on the Roche GS 454 FLX$_+$ platform.

Experimental Setup
(a) DNA from a single cell was extracted;
(b) the DNA sample was digested using MseI as restriction enzyme;
(c) a first oligonucleotide was annealed to the generated overhang. Subsequently, a second oligonucleotide comprising a randomized sequence was annealed to the first oligonucleotide;
(d) the second oligonucleotide was ligated to the ends of MseI fragments;
(e) the overhangs generated by the ligated second oligonucleotide were filled-in;
(f) the fragments were amplified using PCR primers complementary to a third sequence of the second oligonucleotide;
(f') because the second oligonucleotide comprised a cleavage site of a homing endonuclease, i.e. SceI, the amplified fragments were cut subsequently to amplification;
(g) cut fragments were end-repaired and T/A-ligated to the Y-adaptor provided in the Rapid Library Prep Kit of Roche Diagnostics. Sequencing on the GS 454 FLX$_+$ platform was performed as described in the 454 Sequencing System Methods Manuals XLR70Series.

Sequencing

Although the method was performed using the 454FLX platform, the skilled person will appreciate that alternative sequencing methods may be used.

Analysis

Analysis of the sequenced DNA fragments required identification of the randomized sequence and subsequent adapter trimming. Both were performed using an in-house JAVA program.

Briefly, sequences of the second oligonucleotide were identified within reads based on a modified biojava implementation of the smith-waterman algorithm; randomized sequences were written to the read header and adaptor sequences clipped while the MseI restriction site ("TTAA") was retained. Reads where the adaptor and hence also the randomized sequence could not be identified (1-3.5% of all reads) were discarded. Further, reads where discarded with a length less than 20 bp after adaptor trimming (0.7-4.3% of all reads in which an adaptor was identified). A screening for contaminating read sequences from non-human species revealed no contamination and the trimmed-reads were therefore directly mapped against the human genome assembly 19 using the BWA mem algorithm with standard settings (Li and Durbin, Bioinformatics 2009 Jul. 15; 25(14):1754-60). In order to illustrate the ability to distinguish between sequencing errors and real mutations/SNPs using the method of the present invention, those genomic regions with a read coverage of at least 12 were identified. These were then further filtered for regions in which at least 8 reads with identical randomized sequences occurred. From the resulting dataset, 4 regions containing putative SNPs/mutations/sequencing errors were randomly selected. For the shown alignments, all reads containing the same randomized sequence were used.

Results

Using the randomized sequences of reads aligned to the same position of the reference genome allowed to reliably differentiate between sequencing-/amplification errors, single nucleotide polymorphisms and real mutations. In every group of reads sharing the same randomized sequence, single nucleotide variations from the reference were found to be specific to one group of randomized sequences (FIG. 19*a-d*).

The invention claimed is:

1. A method of error-free sequencing of DNA, comprising the steps of:
   (a) providing a sample comprising DNA;
   (b) digesting the DNA with a restriction endonuclease under conditions suitable to obtain DNA fragments of similar length,
      wherein said restriction endonuclease is capable of providing 5' overhangs, wherein the terminal nucleotide of the overhang is phosphorylated or,
      wherein said restriction endonuclease is capable of providing 3' overhangs, wherein the terminal nucleotide of the overhang is hydroxylated on said DNA fragments;
   (c) annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence;
   (d) ligating said second oligonucleotide to said DNA fragment;
   (e) filling in of the generated overhangs;
   (f) amplifying said DNA fragments using a third oligonucleotide comprising a sequence binding to said third sequence of said second oligonucleotide; and
   (g) sequencing said amplified DNA fragments.

2. The method of claim 1, wherein said second oligonucleotide further comprises a fourth sequence comprising a restriction site of a site-specific endonuclease.

3. The method of claim 2, wherein said method further comprises the step (f') wherein a homing endonuclease is added in said step (f').

4. The method of claim 1, wherein said second oligonucleotide is a DNA oligonucleotide, an RNA oligonucleotide or a DNA/RNA oligonucleotide.

5. The method of claim 1, wherein said method further comprises the step (e'), wherein an exonuclease is added in said step (e').

6. The method of claim 5, wherein said exonuclease is an enzyme degrading single-stranded DNA, RNA or DNA/RNA molecules.

7. The method of claim 1, wherein said DNA comprises (i) the genome or transcriptome of a single cell, (ii) chromosome(s) of a single cell, (iii) nucleic acids from exosomes or other microvesicles of a single cell or (iv) fragment(s) or subfraction(s) of the material of any one of items (i) to (iii).

8. The method of claim 1, wherein said DNA comprises (i) the DNA of more than one single cell, (ii) cell-free fetal DNA of more than one single cell, (iii) cell-free DNA of more than one single cell in serum and/or plasma of cancer patients or (iv) fragment(s) or subfraction(s) of the material of any one of items (i) to (iii).

9. The method of claim 1, wherein said restriction endonuclease is MseI or an isoschizomer thereof.

10. The method of claim 1, wherein said randomized sequence comprises 3 to 24 nucleotides.

11. The method of claim 1, wherein said first oligonucleotide has the sequence 5'-TAACTGACdd-3' and/or wherein said second oligonucleotide has the sequence as shown in SEQ ID NO: 1 and/or wherein said third oligonucleotide has the sequence as shown in SEQ ID NO: 2.

12. The method of claim 1, wherein the last 3' nucleotide of the first oligonucleotide is a dd-nucleotide.

* * * * *

SEQUENCE LISTING

<160> NUMBER OF SEQ ID NOS: 139

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (23)..(34)
<223> OTHER INFORMATION: n is a, c, g, or t

<400> SEQUENCE: 1
gctagggata acagggtaat gcnnnnnnnn nnnngtcagt                         40

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
gctagggata acagggtaat gc                                            22

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3
tagggataac agggtaat                                                 18

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
gctagggata acagggtaat gc                                            22

<210> SEQ ID NO 5
<211> LENGTH: 40
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (23)..(34)
<223> OTHER INFORMATION: n is a, c, g, or t

<400> SEQUENCE: 5
gctagggata acagggtaat gcnnnnnnnn nnnngtcagt                         40

<210> SEQ ID NO 6
<211> LENGTH: 36
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature

```
<222> LOCATION: (23)..(31)
<223> OTHER INFORMATION: n is a, c, g, or t

<400> SEQUENCE: 6
gctagggata acagggtaat gcnnnnnnnn ngtcgt                              36

<210> SEQ ID NO 7
<211> LENGTH: 435
<212> TYPE: DNA
<213> ORGANISM: Artificial Sequence
<220> FEATURE:
<223> OTHER INFORMATION: Synthetic oligonucleotide

<400> SEQUENCE: 7
gctagggata acagggtaat gcgtggtcag gggggtcagt taaagtagtt ttggcaaatt    60
ggataaagag tcaagaccca tcagtgtgct gtattcagga aacccatctc atgtgcagag   120
acacacatag gctcaaaata aaggatgga ggaagatcta ccaagcaaat ggaaaacaaa    180
aaaaggcagg ggttgcaatc ctagtctctg ataaaacaga ctttatacca acaaagatca   240
aaagagacaa agaaggccat tacataatgg taaagagatc aattcaacaa gaagagctaa   300
ctatcctaaa tatatatgca cccaatacag gagcacccag attcataaag caagtcctga   360
gtgacctaca aagagactta gactcccaga cattaactga cactctcgtc cttgcattac   420
cctgttatcc ctagc                                                   435

<210> SEQ ID NO 8
<211> LENGTH: 543
<212> TYPE: DNA
<213> ORGANISM: Artificial Sequence
<220> FEATURE:
<223> OTHER INFORMATION: Synthetic oligonucleotide

<400> SEQUENCE: 8
gctagggata acagggtaat gcgcgaaggt aggcgtcagt taaccaagaa aagaggagag    60
aaaatacaaa taagctcaat aaggaacaaa acaggagaca ttacaactga cactatataa   120
atacaaaaga tcattcaagg ctactgtgaa cacctttaca tgcataaact agaaaaccta   180
aaagacatgg ataaattcct ggaaagtaga gaggcatcac attacccaac ttcaaactat   240
actataaggc tatagtcacc aactcagcat ggcactggta taaaaatagg catgtagacc   300
aatgaaacag aaaagagaac ccagacataa agccaaatac agccaaccaa tctttgacaa   360
agcaaacaaa aacataaagt ggggaaagga cgctctattc aacaaatggt gctgggataa   420
ttggcaagcc acatgtagaa gaatgaaact ggatcctcat ctcccctta tacaaaatca    480 acacaaaata gataaaagac ttaactgacc cacaaggata ggcattaccc tgttatccct   540
agc                                                                543

<210> SEQ ID NO 9
<211> LENGTH: 440
<212> TYPE: DNA
<213> ORGANISM: Artificial Sequence
<220> FEATURE:
<223> OTHER INFORMATION: Synthetic oligonucleotide

<400> SEQUENCE: 9
gctagggata acagggtaat gcgtaggaga aaatgtcagt taaatctata aattgtgtgc    60
cacgtgcggt ggctcatgac tgtaatccca gcactttggg agtccgaggt gggcagatca   120
cgaggtcagg agattgagac catcttggct aacacggtga aaccctgtct ctactaaaaa   180
```

```
tacaaaaaca aaattagccg ggtgaggtgg caggcacctg tagtcccagc tactccagag    240
gctgaggtga gagaatggcg tgaacctggg aggcagagct tgcagtgagc tgagattgtg    300
ccactgcact ccagtctggg tgacagagca agactctgtc tcaaaaaaaa aaaaaaaaaa    360
aaaaattcta taaattgtgt tgggcagtat ggccttttta actgacacta aagtcacagc    420
attaccctgt tatccctagc                                                440
```

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10

```
tagggataac agggtaat                                                   18
```

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 11

```
taactataac ggtcctaagg tagcgaa                                         27
```

<210> SEQ ID NO 12
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (29)..(40)
<223> OTHER INFORMATION: n is a, c, g, or t

<400> SEQUENCE: 12

```
agttacgcta gggataacag ggtaatgcnn nnnnnnnnnn gtcagt                    46
```

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 13

```
cgcagttacg ctagggataa cag                                             23
```

<210> SEQ ID NO 14
<211> LENGTH: 50
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (32)..(43)
<223> OTHER INFORMATION: n is a, c, g, or t

<400> SEQUENCE: 14

```
cgcagttacg ctagggataa cagggtaatg cnnnnnnnnn nnngatcagt                50
```

<210> SEQ ID NO 15
<211> LENGTH: 91
<212> TYPE: DNA
<213> ORGANISM: Artificial Sequence
<220> FEATURE:
<223> OTHER INFORMATION: Synthetic oligonucleotide

<400> SEQUENCE: 15
gaagagggga gtgggaagta gaggctgagt gatttaggta tttccaataa tcaatagcaa     60
gaccactgtg agctgaatac atcgggttat c                                    91

<210> SEQ ID NO 16
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 16
gaagagggga gtgggaagtg aggctgagtg atttaggtat ttccaataat caatagcaag     60
accactgtga gctgaataca tcgggttatc                                      90

<210> SEQ ID NO 17
<211> LENGTH: 91
<212> TYPE: DNA
<213> ORGANISM: Artificial Sequence
<220> FEATURE:
<223> OTHER INFORMATION: Synthetic oligonucleotide

<400> SEQUENCE: 17
gaagaggggg agtgggaagt gaggctgagt gatttaggta tttccaataa tcaatagcaa     60
gaccactgtg agctgaatac atcgggttat c                                    91

<210> SEQ ID NO 18
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 18
atgagtggga tatgggaagt gaggctgagt gatttaggta tttccatatc aatagcaaga     60
ccactgtgag ctgaatacat caggttatc                                       89

<210> SEQ ID NO 19
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 19
atgagtggga tatgggaagt gaggctgagt gatttaggta tttccatatc aatagcaaga     60
ccactgtgag ctgaatacat caggttatc                                       89

<210> SEQ ID NO 20
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 20
atgagtggga tatgggaagt gaggctgagt gatttaggta tttccatatc aatagcaaga    60
ccactgtgag ctgaatacat caggttatc                                      89

<210> SEQ ID NO 21
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 21
atgagtggga tatgggaagt gaggctgagt gatttaggta tttccatatc aatagcaaga    60
ccactgtgag ctgaatacat caggttatc                                      89

<210> SEQ ID NO 22
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 22
atgagtggga tatgggaagt gaggctgagt gatttaggta tttccatatc aatagcaaga    60
ccactgtgag ctgaatacat caggttatc                                      89

<210> SEQ ID NO 23
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 23
atgagtggga tatgggaagt gaggctgagt gatttaggta tttccatatc aatagcaaga    60
ccactgtgag ctgaatacat caggttatc                                      89

<210> SEQ ID NO 24
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 24
atgagtggga tatgggaagt gaggctgagt gatttaggta tttccatatc aatagcaaga    60
ccactgtgag ctgaatacat caggttatc                                      89

<210> SEQ ID NO 25
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 25
atgagtggga tatgggaagt gaggctgagt gatttaggta tttccatatc aatagcaaga    60
ccactgtgag ctgaatacat caggttatc                                      89

<210> SEQ ID NO 26
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 26
atgagtggga tatgggaagt gaggctgagt gatttaggta tttccatatc aatagcaaga    60
ccactgtgag ctgaatacat caggttatc                                      89

<210> SEQ ID NO 27
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 27
gataaatatg aacactgcac cgtgaaattc tgtgcctcga agacaggctc gctattttag    60
aagaggg                                                              67

<210> SEQ ID NO 28
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 28
gataaatatg aacactgcac cgtgaaattc tgtgcctccg aagacaggct cgctattttt    60
agaaagaggg                                                           70

<210> SEQ ID NO 29
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 29
gataaatatg aacactgcac cgtgaaattc tgtgcctccg aagacaggct cgctattttt    60
agaaagaggg                                                           70

<210> SEQ ID NO 30
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 30
gataaatatg aacactgcac cgtgaaattc tgtgcctccg aagacaggct cgctattttt    60
agaaagaggg                                                           70

<210> SEQ ID NO 31
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 31
gataaatatg aacactgcac cgtgaaattc tgtgcctccg aagacaggct cgctattttt    60
agaaagaggg                                                           70

<210> SEQ ID NO 32
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 32
gataaatatg aacactgcac cgtgaaattc tgtgcctccg aagacaggct cgctatttttt    60 agaaagaggg                                                            70

<210> SEQ ID NO 33
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 33
gataaatatg aacactgcac cgtgaaattc tgtgcctccg aagacaggct cgctatttttt    60 agaaagaggg                                                            70

<210> SEQ ID NO 34
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 34
gataaatatg aacactgcac cgtgaaattc tgtgcctccg aagacaggct cgctatttttt    60 agaaagaggg                                                            70

<210> SEQ ID NO 35
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 35
gataaatatg aacactgcac cgtgaaattc tgtgcctccg aagacaggct cgctatttttt    60 agaaagaggg                                                            70

<210> SEQ ID NO 36
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 36
gataaatatg aacactgcac cgtgaaattc tgtgcctccg aagacaggct cgctatttttt    60 agaaagaggg                                                            70

<210> SEQ ID NO 37
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 37
gataaatatg aacactgcac cgtgaaattc tgtgcctccg aagacaggct cgctattttt    60
agaaagaggg                                                            70

<210> SEQ ID NO 38
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 38
gataaatatg aacactgcac cgtgaaattc tgtgcctccg aagacaggct cgctattttt    60
agaaagaggg                                                            70

<210> SEQ ID NO 39
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 39
gataaatatg aacactgcac cgtgaaattc tgtgcctccg aagacaggct cgctattttt    60
agaaagaggg                                                            70

<210> SEQ ID NO 40
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 40
gataaatatg aacactgcac cgtgaaattc tgtgcctccg aagacaggct cgctattttt    60
agaaagaggg                                                            70

<210> SEQ ID NO 41
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 41
agacgtttta agcactgcac tgtgaaattc tgtgcctccg aagacaggct cgctattttt    60
agaaagaggg                                                            70

<210> SEQ ID NO 42
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 42
agacgtttaa gcactgcact gtgaaattct gtgcctccga agacaggctc gctattttta    60
gaaagaggg                                                             69

<210> SEQ ID NO 43
<211> LENGTH: 70
<212> TYPE: DNA

```
<213> ORGANISM: Artificial Sequence
<220> FEATURE:
<223> OTHER INFORMATION: Synthetic oligonucleotide

<400> SEQUENCE: 43
agacgtttta agcactgcac tgtgaaattc tgtgcctccg aagacaggct cgctattttt      60
agaaagaggg                                                            70

<210> SEQ ID NO 44
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 44
taaatagggt ttcactgcac tgtgaaattc tgtgcctccg aagacaggct cgctattttt      60
agaaagaggg                                                            70

<210> SEQ ID NO 45
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 45
agcgggggtt ggaggtaagg tggtgaataa cgggtttccc aaa                       43

<210> SEQ ID NO 46
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 46
agcgggggtt ggaggtaagg tggtgataac gggtttccca aaacaggtga acggacgtac      60
gggagtaggg ac                                                         72

<210> SEQ ID NO 47
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 47
agcgggggtt ggaggtaagg tggtgataac gggtttccca aaaca                     45

<210> SEQ ID NO 48
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 48
agcgggggtt ggaggtaagg tggtgataac gggtttccca aaacaggtga acggacgtac      60
ggga                                                                  64

<210> SEQ ID NO 49
<211> LENGTH: 64
```

```
<212> TYPE: DNA
<213> ORGANISM: Artificial Sequence
<220> FEATURE:
<223> OTHER INFORMATION: Synthetic oligonucleotide

<400> SEQUENCE: 49
agcgggggtt ggaggtaagg tggtgataac gggtttccca aaacaggtga acggacgtac      60
ggga                                                                  64

<210> SEQ ID NO 50
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 50
agcgggggtt ggaggtaagg tggtgataac gggtttccca aaacaggtga acggacgtac      60
gggagtaggg ac                                                         72

<210> SEQ ID NO 51
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 51
agcgggggtt ggaggtaagg tggtgataac gggtttccca aaacaggtga acggacgtac      60
gggagtaggg ac                                                         72

<210> SEQ ID NO 52
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 52
agcgggggtt ggaggtaagg tggtgataac gggtttccca aaacaggtga acggacgtac      60
gggagtaggg ac                                                         72

<210> SEQ ID NO 53
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 53
agcgggggtt ggaggtaagg tggtgataac gggtttccca aaacaggtga acggacgtac      60
gggagtaggg ac                                                         72

<210> SEQ ID NO 54
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 54
agcgggggtt ggaggtaagg tggtgataac gggtttccca aaacaggtga acggacgtac      60
``` ggga                                                                    64

<210> SEQ ID NO 55
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 55
agcgggggtt ggaggtaagg tggtgataac gggtttccca aaaca              45

<210> SEQ ID NO 56
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 56
agcgggggtt ggaggtaagg tggtgataac gggtttccca aa                 42

<210> SEQ ID NO 57
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 57
agcgggggtt ggaggtaagg tggtgataac gggtttccca aaacaggtga acggacgtac     60
gggagta                                                               67

<210> SEQ ID NO 58
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 58
agcgggggtt ggaggtaagg tggtgataac gggtttccca aa                 42

<210> SEQ ID NO 59
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 59
agcgggggtt ggaggtaagg tggtgataac gggtttccca aaacaggtga acggacgtac     60
gggagtaggg ac                                                         72

<210> SEQ ID NO 60
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 60
agcgggggtt ggaggtaagg tggtgataac gggtttccca aa                 42

```
<210> SEQ ID NO 61
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 61
agcgggggtt ggaggtaagg tggtgataac gggtttccca aaacaggtga acggacgtac      60
gggagtaggg ac                                                         72

<210> SEQ ID NO 62
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 62
agcgggggtt ggaggtaagg tggtgataac gggtttccca aaacaggtga acggacgtac      60
gggagtaggg a                                                          71

<210> SEQ ID NO 63
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 63
agcgggggtt ggaggtaagg tggtgataac gggtttccca aaacaggtga acggacgtac      60
ggga                                                                  64

<210> SEQ ID NO 64
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 64
agcgggggtt ggaggtaagg tggtgataac gggtttccca aaacaggtga acggacgtac      60
gggagtaggg ac                                                         72

<210> SEQ ID NO 65
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 65
agcgggggtt ggaggtaagg tggtgataac gggtttccca aaacaggtga acggacgtac      60
gggagta                                                               67

<210> SEQ ID NO 66
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 66
```

```
agcgggggtt ggaggtaagg tggtgataac gggtttccca aaacaggtga acggacgtac    60
gggagtaggg ac                                                        72

<210> SEQ ID NO 67
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 67
agcgggggtt ggaggtaagg tggtgataac gggtttccca aa                       42

<210> SEQ ID NO 68
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 68
agcgggggtt ggaggtaagg tggtgataac gggtttccc                           39

<210> SEQ ID NO 69
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 69
agcggggttg gaggtaaggt ggtgataacg ggtttcccaa aacaggtgaa cggacgtacg    60
ggagtaggga c                                                         71

<210> SEQ ID NO 70
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 70
agcggggttg gaggtaaggt ggtgataacg ggtttcccaa aacaggtgaa cggacgtacg    60
ggagtaggga c                                                         71

<210> SEQ ID NO 71
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 71
atagactagg cgaggtaagg tggtgacaac gggtttccca aaacaggtga acggacatac    60
gggagtaggg ac                                                        72

<210> SEQ ID NO 72
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 72
```
atagactagg cgaggtaagg tggtgacaac gggtttccca aaacaggtga acggacatac    60

<210> SEQ ID NO 73
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 73
atagactagg cgaggtaagg tggtgacaac gggtttccca aaacaggtga acggacatac    60
gggagtaggg ac                                                        72

<210> SEQ ID NO 74
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 74
atagactagg cgaggtaagg tggtgacaac gggtttccca aaacaggtga acggacatac    60
gggataggga c                                                         71

<210> SEQ ID NO 75
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 75
atagactagg cgaggtaagg tggtgacaac gggtttccca aaacaggtga acggacatac    60
gggagtaggg ac                                                        72

<210> SEQ ID NO 76
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 76
atagactagg cgaggtaagg tggtgacaac gggtttccca aaacaggtga acggacatac    60
gggagtaggg ac                                                        72

<210> SEQ ID NO 77
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 77
atagactagg cgaggtaagg tggtgacaac gggtttccca aaacaggtga acggacatac    60
gggagtaggg ac                                                        72

<210> SEQ ID NO 78
<211> LENGTH: 72
<212> TYPE: DNA
<213> ORGANISM: Artificial Sequence
<220> FEATURE:

<223> OTHER INFORMATION: Synthetic oligonucleotide

<400> SEQUENCE: 78
atagactagg cgaggtaagg tggtgacaac gggtttccca aaacaggtga acggacatac    60
gggagtaggg ac    72

<210> SEQ ID NO 79
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 79
atagactagg cgaggtaagg tggtgacaac gggtttccca aaacaggtga acggacatac    60
gggagtaggg ac    72

<210> SEQ ID NO 80
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 80
atagactagg cgaggtaagg tggtgacaac gggtttccca aaacaggtga acggacatac    60
gggataggga c    71

<210> SEQ ID NO 81
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 81
atagactagg cgaggtaagg tggtgacaac gggtttccca aaacaggtga acggacatac    60
gggagtaggg ac    72

<210> SEQ ID NO 82
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 82
atagactagg cgaggtaagg tggtgacaac gggtttccca aaacaggtga acggacatac    60
gggagtaggg ac    72

<210> SEQ ID NO 83
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 83
atagactagg cgaggtaagg tggtgacaac gggtttccca aaacaggtga acggacatac    60
gggagtaggg ac    72

```
<210> SEQ ID NO 84
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 84
atagactagg cgaggtaagg tggtgacaac gggtttccca aaacaggtga acggacatac    60
gggagtaggg ac                                                        72

<210> SEQ ID NO 85
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 85
atagactagg cgaggtaagg tggtgacaac gggtttccca aaacaggtga acggacatac    60
gggagtaggg ac                                                        72

<210> SEQ ID NO 86
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 86
atagactagg cgaggtaagg tggtgacaac gggtttccca aaacaggtga acggacatac    60
gggagtaggg ac                                                        72

<210> SEQ ID NO 87
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 87
atagactagg cgaggtaagg tggtgacaac gggtttccca aaacaggtga acggacatgc    60
gggagtaggg ac                                                        72

<210> SEQ ID NO 88
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 88
atagactagg cgaggtaagg tggtgacaac gggtttccca aaacaggtga acggacatac    60
gggagtaggg ac                                                        72

<210> SEQ ID NO 89
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 89
```
atagactagg cgaggtaagg tggtgacaac gggtttccca aaacaggtga acggacatac    60
gggagtaggg ac                                                        72

<210> SEQ ID NO 90
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 90
atagactagg cgaggtaagg tggtgacaac gggtttccca aaacaggtga acggacatac    60
gggagtaggg ac                                                        72

<210> SEQ ID NO 91
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 91
atagactagg cgaggtaagg tggtgacaac gggtttccca aaacaggtga acggacatac    60
gggagtaggg ac                                                        72

<210> SEQ ID NO 92
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 92
atagactagg cgaggtaagg tggtgacaac gggtttccca aaacaggtga acggacatac    60
gggagtaggg ac                                                        72

<210> SEQ ID NO 93
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 93
atagactagg cgaggtaagg tggtgacaac gggtttccca aaacaggtga acggacatac    60
gggagtaggg ac                                                        72

<210> SEQ ID NO 94
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 94
atagactagg cgaggtaagg tggtgacaac gggtttccca aaacaggtga acggacatac    60
gggagtaggg ac                                                        72

<210> SEQ ID NO 95
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 95
atagactagg cgaggtaagg tggtgacaac gggtttccca gaacaggtga acggacatac    60
gggagtaggg ac    72

<210> SEQ ID NO 96
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 96
atatttaaag cttatcccct gtgtgccttg gtggagttgg aaggaatgat ttgtgtctgg    60
gagggg    66

<210> SEQ ID NO 97
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 97
atatttaaag cttatcccct gtgtgccttg gtggagttgg aaggaatgat ttgtgtctgg    60
gagggg    66

<210> SEQ ID NO 98
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 98
atatttaaag ctggtggagt tggaaggaat gatttgtgtc tggagggg    48

<210> SEQ ID NO 99
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 99
atatttaaag ctccctgtg tgccttggtg gagttggagg aatgatttgt gtctgggagg    60
gg    62

<210> SEQ ID NO 100
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 100
atatttaaag cttatcccct gtgtgccttg gtggagttgg aggaatgatt tgtgtctgga    60
gggg    64

<210> SEQ ID NO 101

```
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 101
atatttaaag cttatcccct gtgtgccttg gtggagttgg aggaatgatt tgtgtctgga      60
gggg                                                                  64

<210> SEQ ID NO 102
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 102
atatttaaag cttatcccct gtgtgccttg gtggagttgg aggaatgatt tgtgtctgga      60
gggg                                                                  64

<210> SEQ ID NO 103
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 103
atatttaaag cttatccccc tgtgtgcctt ggtggagttg gaggaatgat ttgtgtctgg      60
agggg                                                                 65

<210> SEQ ID NO 104
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 104
atatttaaag cttatcccct gtgtgccttg gtggagttgg aaggaatgat ttgtgtctgg      60
agggg                                                                 65

<210> SEQ ID NO 105
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 105
atatttaaag cttatcccct gtgtgccttg gtggagttgg aaggaatgat ttgtgtctgg      60
agggg                                                                 65

<210> SEQ ID NO 106
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 106
atatttaaag cttatcccct gtgtgccttg gtggagttgg aaggaatgat ttgtgtctgg      60
``` aggggg                                                              65

<210> SEQ ID NO 107
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 107
atatttaaag cttatcccct gtgtgccttg gtggagttgg aaggaatgat ttgtgtctgg    60
aggggg                                                              65

<210> SEQ ID NO 108
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 108
atatttaaag cttatcccct gtgtgccttg gtggagttgg aaggaatgat ttgtgtctgg    60
aggggg                                                              65

<210> SEQ ID NO 109
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 109
atatttaaag cttatcccct gtgtgccttg gtggagttgg aaggaatgat ttgtgtctgg    60
aggggg                                                              65

<210> SEQ ID NO 110
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 110
atatttaaag cttatcccct gtgtgccttg gtggagttgg aaggaatgat ttgtgtctgg    60
aggggg                                                              65

<210> SEQ ID NO 111
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 111
atatttaaag cttatcccct gtgtgccttg gtggagttga ggaatgattt gtgtctggga    60
gggg                                                                64

<210> SEQ ID NO 112
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 112
atatttaaag ctcccctgtg tgccttggtg gagttgagga atgatttgtg tctggagggg    60

<210> SEQ ID NO 113
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 113
atatttaaag cttatcccct gtgtgccttg gtggagttga ggaatgattt gtgtctggag    60
ggg    63

<210> SEQ ID NO 114
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 114
atatttaaag cttatcccct gtgtgccttg gtggagttga ggaatgattt gtgtctggag    60
ggg    63

<210> SEQ ID NO 115
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 115
atgaatgcag tttgtgtgcc ttggtggagt tggaaggagt gatttgcgtc tgggagggg    59

<210> SEQ ID NO 116
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 116
atgaatgcag tttgtgtgcc ttggtggagt tggaaggagt gatttgcgtc tgggaggg    58

<210> SEQ ID NO 117
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 117
atgaatgcag tttatcccct gtgtgccttg gtggagttgg aaggagtgat ttgcgtctgg    60
gaggg    65

<210> SEQ ID NO 118
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 118
atgaatgcag tttatcccct gtgtgccttg gtggagttgg aaggagtgat ttgcgtctgg    60
gaggg    65

<210> SEQ ID NO 119
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 119
atgaatgcag tttatcccct gtgtgccttg gtggagttgg aaggagtgat ttgcgtctgg    60
gaggg    65

<210> SEQ ID NO 120
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 120
atgaatgcag tttatcccct gtgtgccttg gtggagttgg aaggagtgat ttgcgtctgg    60
gaggg    65

<210> SEQ ID NO 121
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 121
atgaatgcag tttatcccct gtgtgccttg gtggagttgg aaggagtgat ttgcgtctgg    60
gaggg    65

<210> SEQ ID NO 122
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 122
atgaatgcag tttatcccct gtgtgccttg gtggagttgg aaggagtgat ttgcgtctgg    60
gaggg    65

<210> SEQ ID NO 123
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 123
atgaatgcag tttatcccct gtgtgccttg gtggagttgg aaggagtgat ttgcgtctgg    60
gaggg    65

<210> SEQ ID NO 124

```
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 124
atgaatgcag ttttggtgga gttggaagga gtgatttgcg tctggaggg              49

<210> SEQ ID NO 125
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 125
atgaatgcag ttttggtgga gttggaagga gtgatttgcg tctggaggg              49

<210> SEQ ID NO 126
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 126
atgaatgcag ttttggtgga gttggaagga gtgatttgcg tctggagggg             50

<210> SEQ ID NO 127
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 127
atgaatgcag tttatcccct gtgtgccttg gtggagttgg aaggagtgat ttgcgtctgg  60
agggg                                                              65

<210> SEQ ID NO 128
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 128
atgaatgcag tttatcccct gtgtgccttg gtggagttgg aaggagtgat ttgcgtctgg  60
agggg                                                              65

<210> SEQ ID NO 129
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 129
atgaatgcag tttatcccct gtgtgccttg gtggagttgg aaggagtgat ttgcgtctgg  60
agggg                                                              65

<210> SEQ ID NO 130
<211> LENGTH: 65
```

<212> TYPE: DNA
<213> ORGANISM: Artificial Sequence
<220> FEATURE:
<223> OTHER INFORMATION: Synthetic oligonucleotide

<400> SEQUENCE: 130
atgaatgcag tttatcccct gtgtgccttg gtggagttgg aaggagtgat ttgcgtctgg      60
agggg                                                                  65

<210> SEQ ID NO 131
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 131
atgaatgcag tttatcccct gtgtgccttg gtggagttgg aaggagtgat ttgcgtctgg      60
agggg                                                                  65

<210> SEQ ID NO 132
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 132
atgaatgcag tttatcccct gtgtgccttg gtggagttgg aaggagtgat ttgcgtctgg      60
agggg                                                                  65

<210> SEQ ID NO 133
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 133
atgaatgcag tttatcccct gtgtgccttg gtggagttgg aaggagtgat ttgcgtctgg      60
agggg                                                                  65

<210> SEQ ID NO 134
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 134
atgaatgcag tttatcccct gtgtgccttg gtggagttgg aaggagtgat ttgcgtctgg      60
agggg                                                                  65

<210> SEQ ID NO 135
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 135
atgaatgcag tttatcccct gtgtgccttg gtggagttgg aaggagtgat tttgcgtctg      60

```
gagggg                                                              66

<210> SEQ ID NO 136
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 136
atgaatgcag tttatccoct gtgtgccttg gtggagttgg aaggagtgat ttgcgtctgg   60
agggg                                                               65

<210> SEQ ID NO 137
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 137
atgaatgcag tttatccoct gtgtgccttg gtggagttgg aaggagtgat ttgcgtctgg   60
agggg                                                               65

<210> SEQ ID NO 138
<211> LENGTH: 92
<212> TYPE: DNA
<213> ORGANISM: Artificial Sequence
<220> FEATURE:
<223> OTHER INFORMATION: Synthetic oligonucleotide

<400> SEQUENCE: 138
gaagagggga gtgggaaggt agaggctgag tgatttaggt atttccaata atcaatagca   60
agaccactgt gagctgaata catcgggtta tc                                 92

<210> SEQ ID NO 139
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 139
gaagagggga gtgggaagtg aggctgagtg atttaggtat ttccataatc aatagcaaga   60
ccactgtgag ctgaatacat cgggttatc                                     89
```